(12) United States Patent
Jansen et al.

(10) Patent No.: US 9,962,170 B2
(45) Date of Patent: May 8, 2018

(54) METHOD AND DEVICES FOR TREATING SPINAL STENOSIS

(75) Inventors: Lex P. Jansen, Pleasanton, CA (US); John W. Davis, Sunnyvale, CA (US); John T. To, Newark, CA (US); Singfatt Chin, Pleasanton, CA (US); Myra I. L. Fabro, San Jose, CA (US)

(73) Assignee: Spine View, Inc., Fremont, CA (US)

( * ) Notice: Subject to any disclaimer, the term of this patent is extended or adjusted under 35 U.S.C. 154(b) by 148 days.

(21) Appl. No.: 12/953,278

(22) Filed: Nov. 23, 2010

(65) Prior Publication Data

US 2011/0288553 A1 Nov. 24, 2011

Related U.S. Application Data

(63) Continuation of application No. PCT/US2009/044989, filed on May 22, 2009.

(60) Provisional application No. 61/055,909, filed on May 23, 2008, provisional application No. 61/084,200, filed on Jul. 28, 2008.

(51) Int. Cl.
*A61B 17/16* (2006.01)

(52) U.S. Cl.
CPC ...... *A61B 17/1671* (2013.01); *A61B 17/1615* (2013.01); *A61B 17/1622* (2013.01); *A61B 17/1633* (2013.01); *A61B 17/1637* (2013.01); *A61B 17/162* (2013.01); *A61B 17/1617* (2013.01); *A61B 17/1628* (2013.01); *A61B 17/1644* (2013.01); *A61B 17/1697* (2013.01)

(58) Field of Classification Search
CPC . A61B 17/1671; A61B 17/1757; A61B 17/16; A61B 17/1637; A61B 17/320016
USPC .................................. 606/79–86 R
See application file for complete search history.

(56) References Cited

U.S. PATENT DOCUMENTS

| | | | | |
|---|---|---|---|---|
| 5,195,541 A | * | 3/1993 | Obenchain | 128/898 |
| 5,484,437 A | * | 1/1996 | Michelson | 606/86 A |
| 6,494,195 B2 | * | 12/2002 | Perry et al. | 124/84 |
| 6,520,907 B1 | * | 2/2003 | Foley et al. | 600/114 |
| 6,558,390 B2 | * | 5/2003 | Cragg | 606/80 |
| 2006/0206118 A1 | * | 9/2006 | Kim et al. | 606/86 |

FOREIGN PATENT DOCUMENTS

EP 0995402 A2 * 10/1999 ............. A61B 17/16

* cited by examiner

*Primary Examiner* — Zade Coley
(74) *Attorney, Agent, or Firm* — Ross M Carothers

(57) ABSTRACT

Systems and methods for treating spinal stenosis include endoscopic access devices and bone removal devices used to perform a foraminotomy or other bone removal procedures. Some of the bone removal devices include expandable members which may be used to control the forced exerted and/or position of the bone removal mechanism, and to protect neurovascular structures and other soft tissue structures from the bone removal mechanism. Other bone removal devices include a trephine with a viewing window and a guide wire lumen used to position the trephine at a target tissue site using an anchored wire. The viewing window may be used to monitor structures or tissues adjacent to the target tissue site.

16 Claims, 24 Drawing Sheets

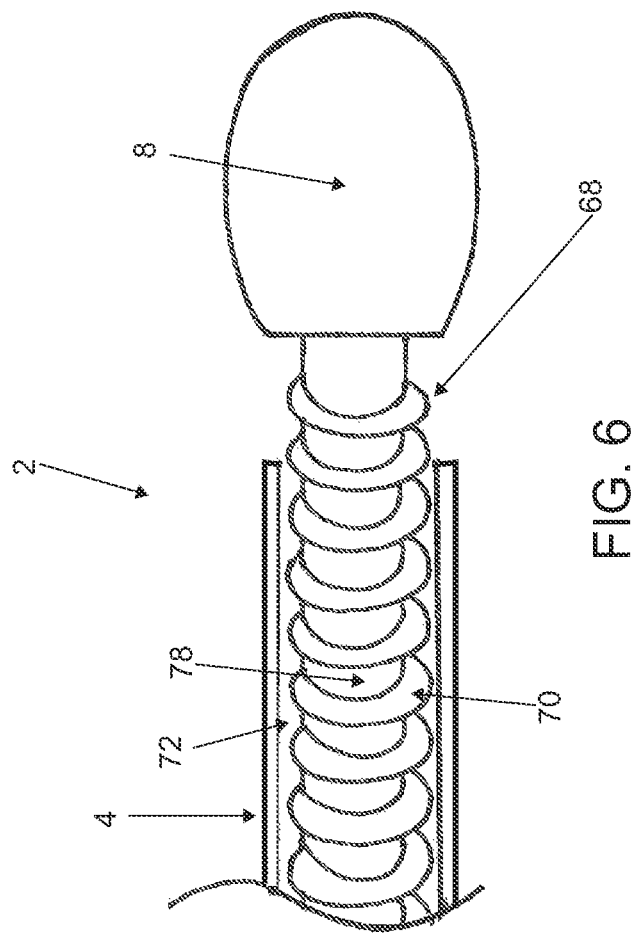

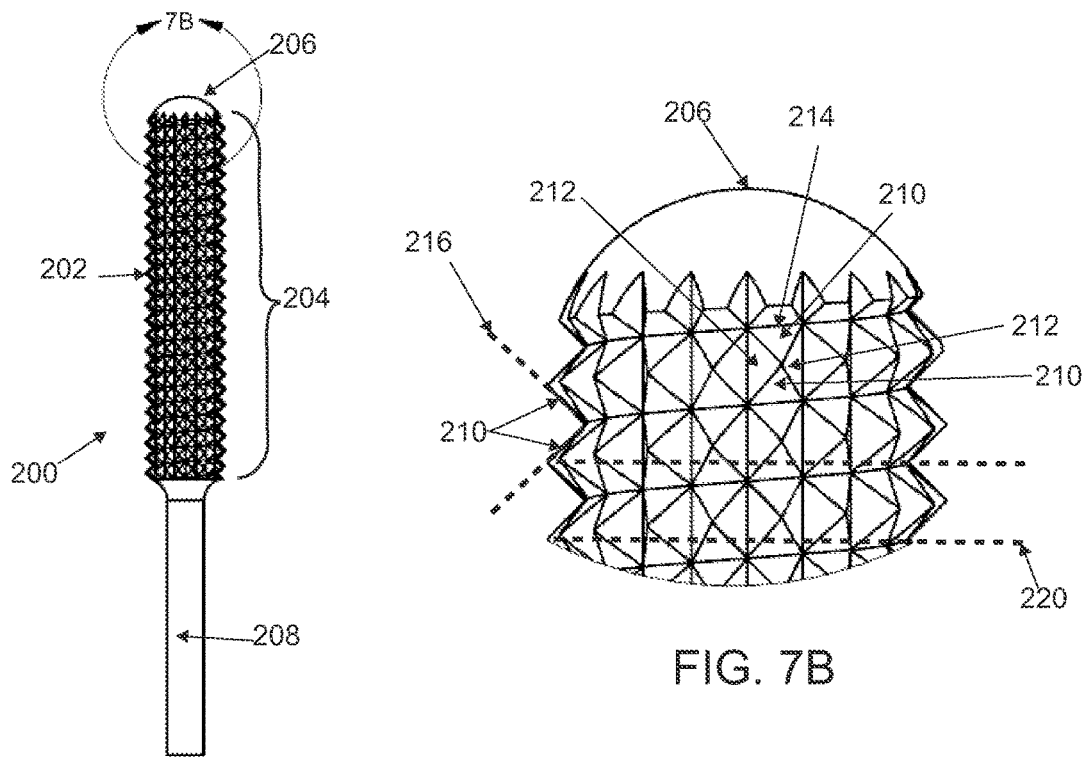
FIG. 7A
FIG. 7B
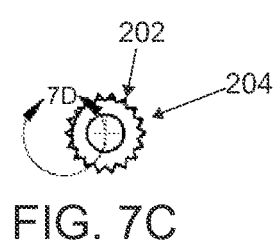
FIG. 7C
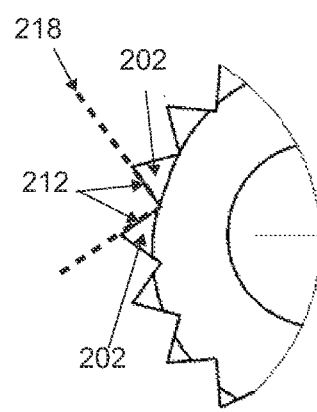
FIG. 7D

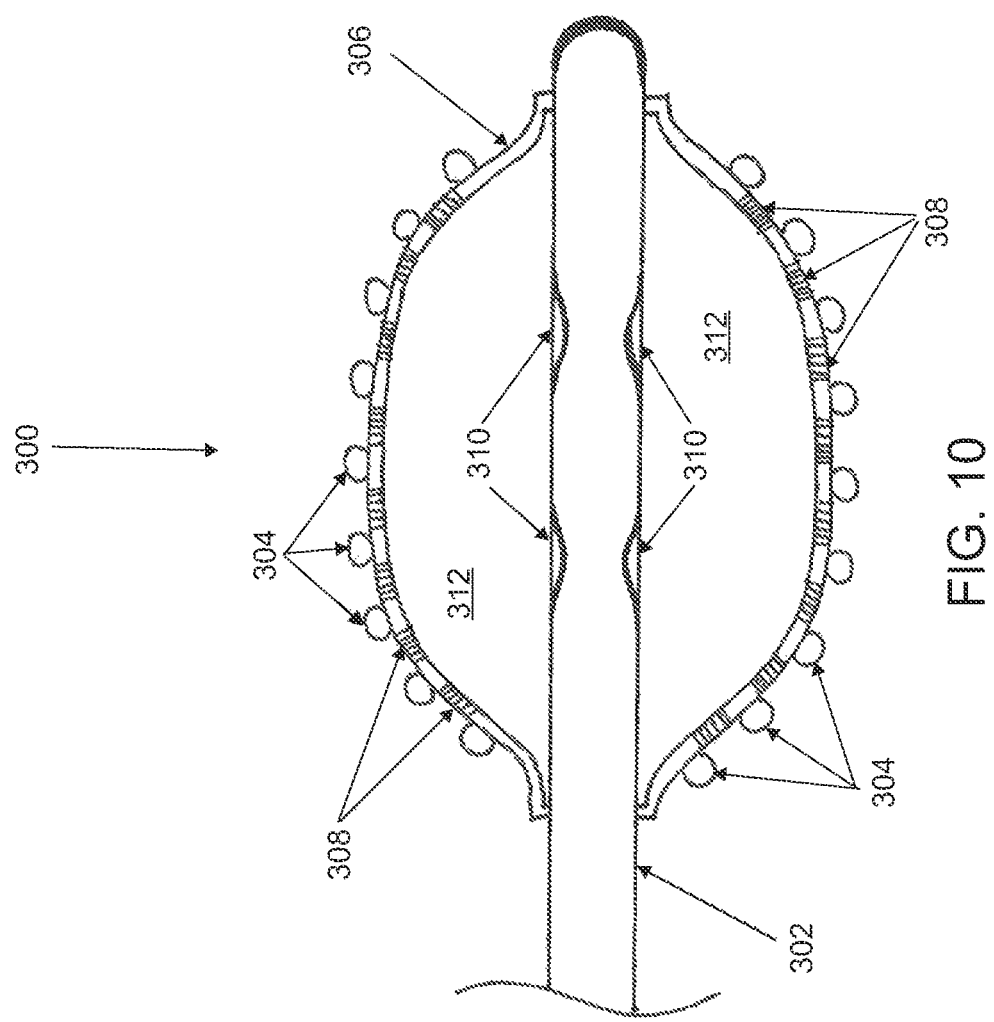

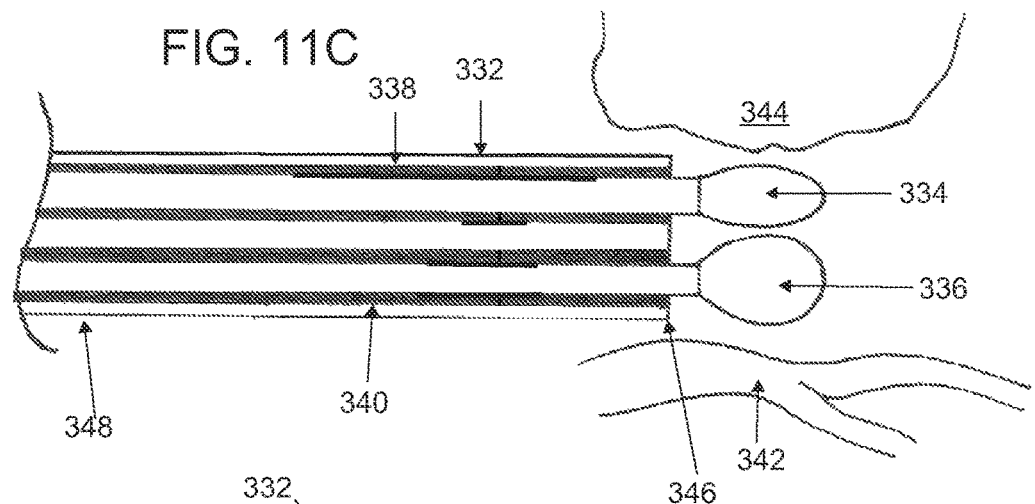
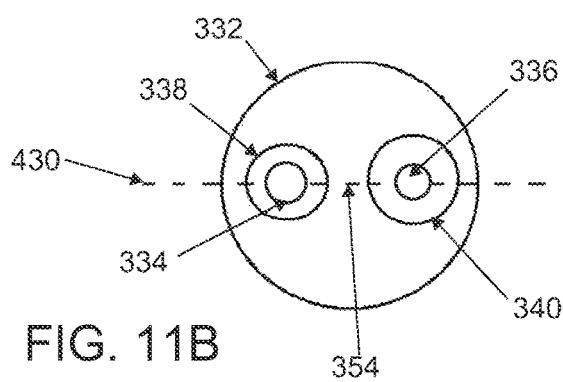
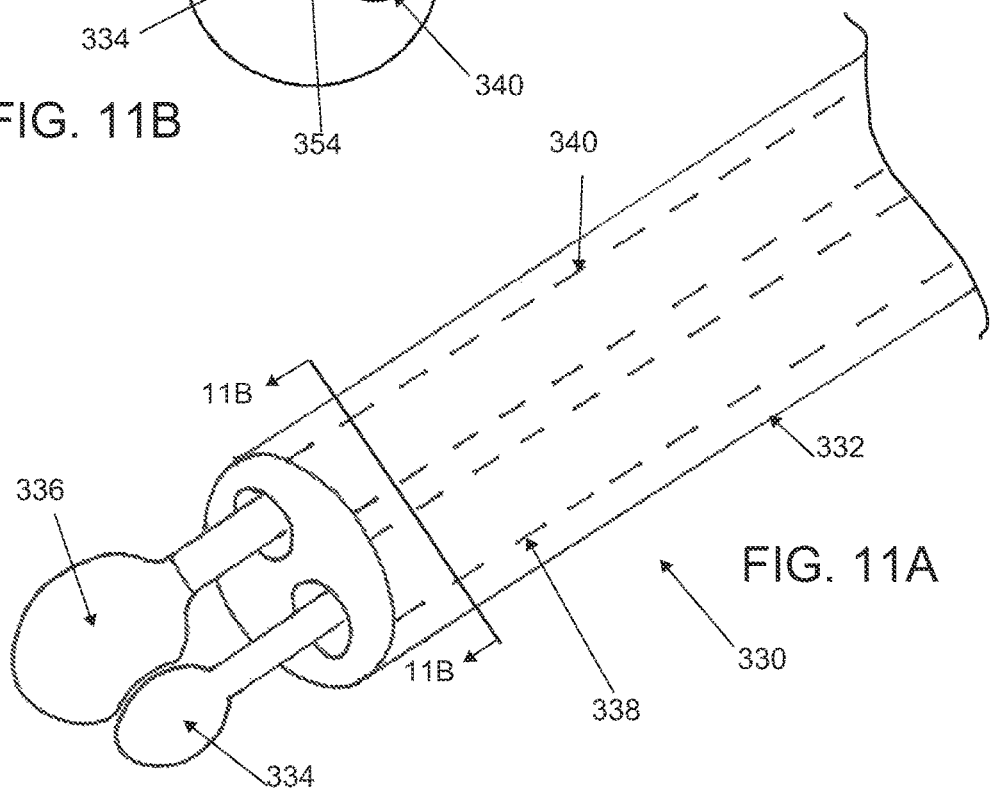

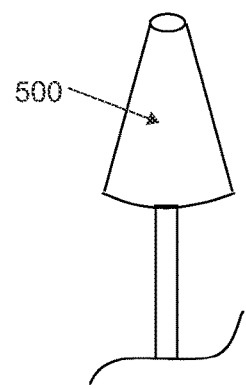
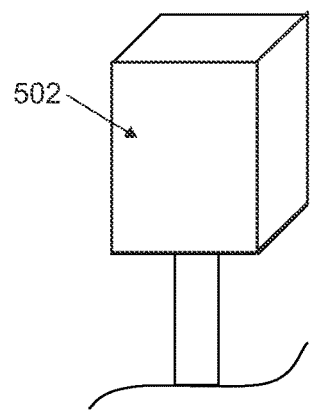
FIG. 18A   FIG. 18B
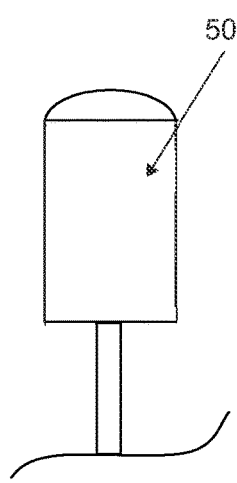
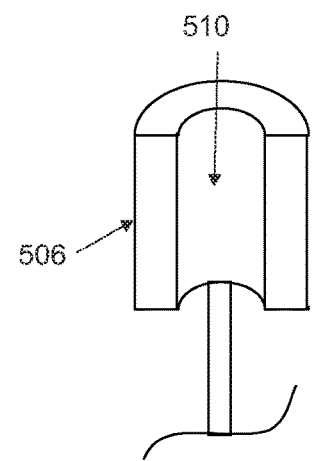
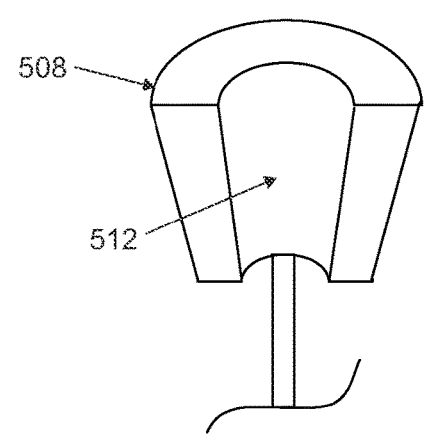
FIG. 18C   FIG. 18D   FIG. 18E

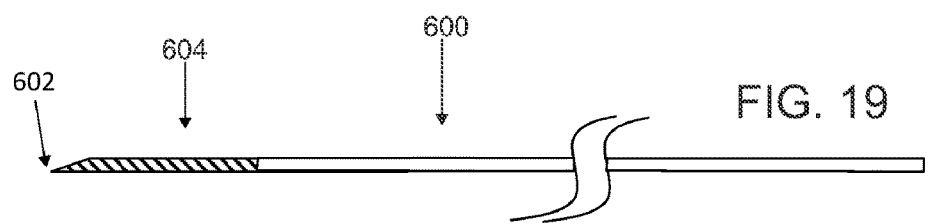
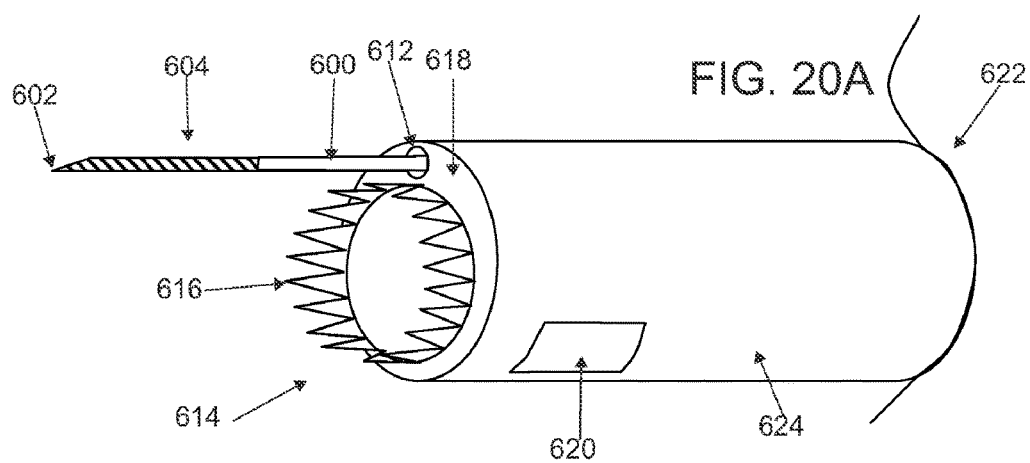
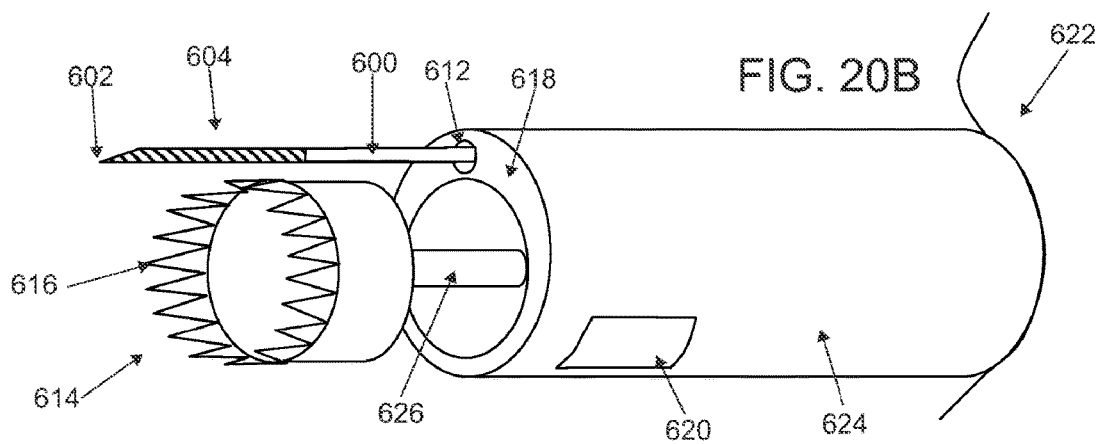

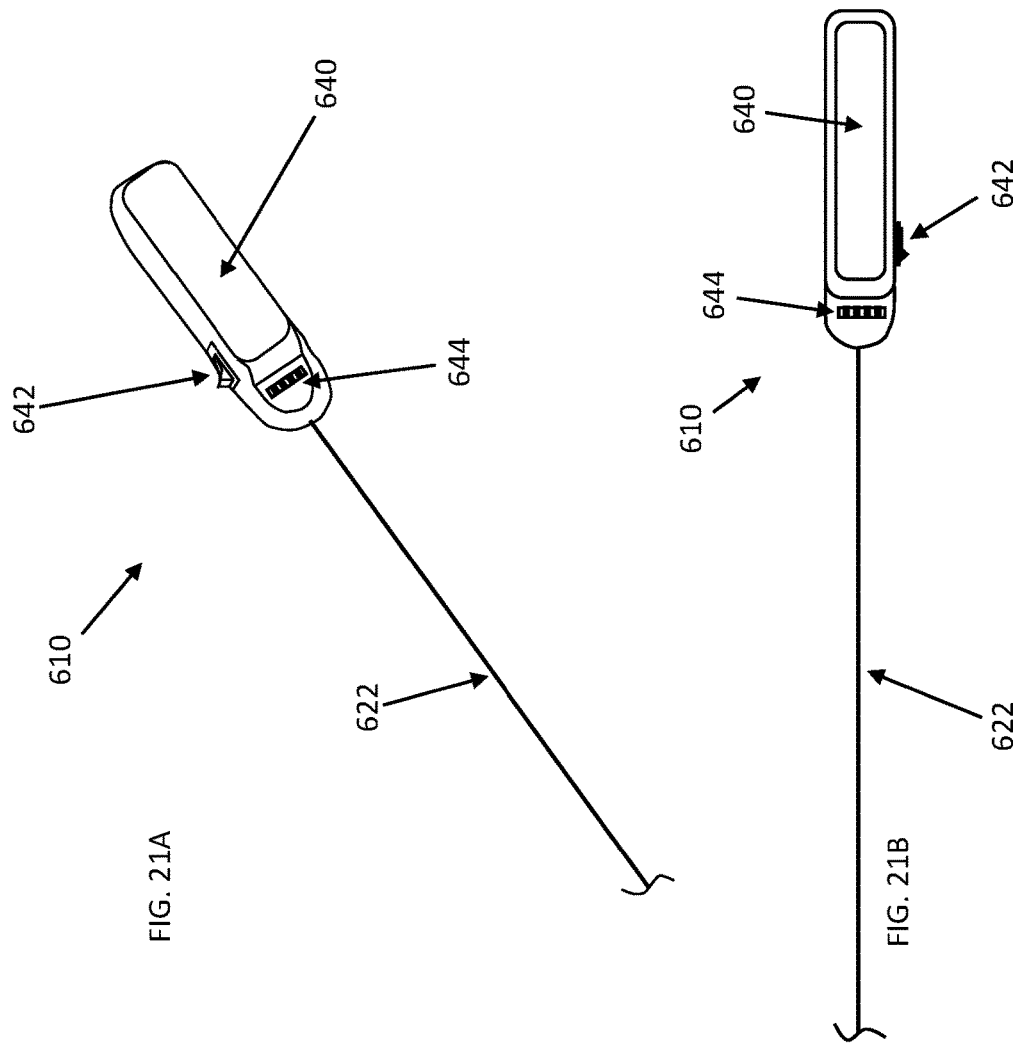

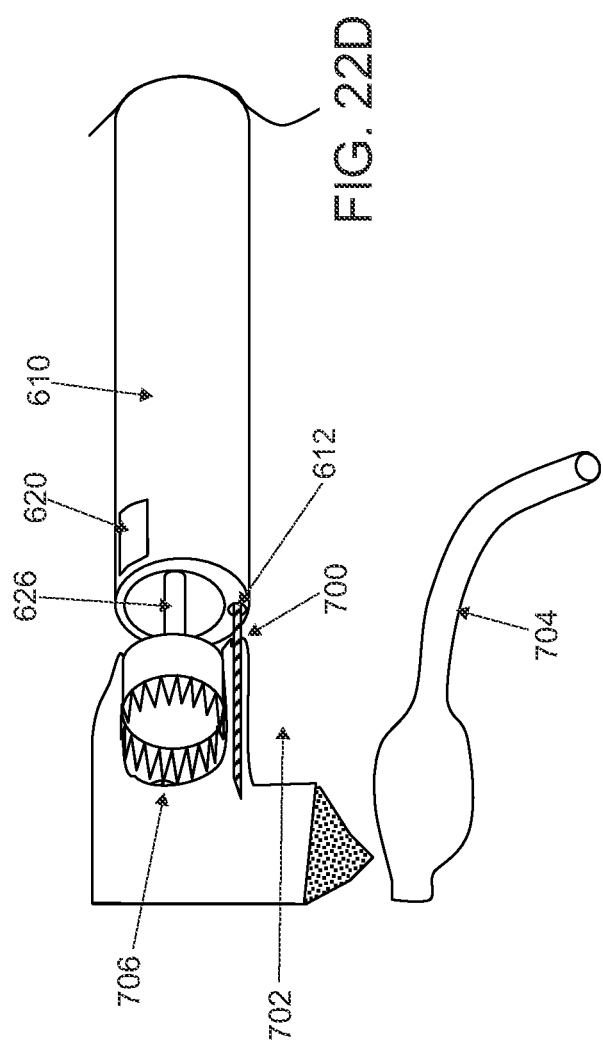

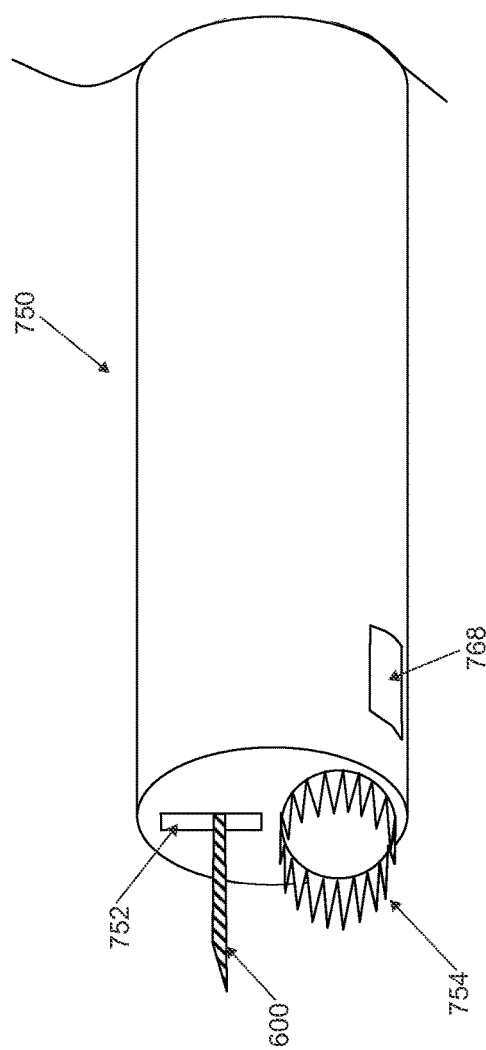
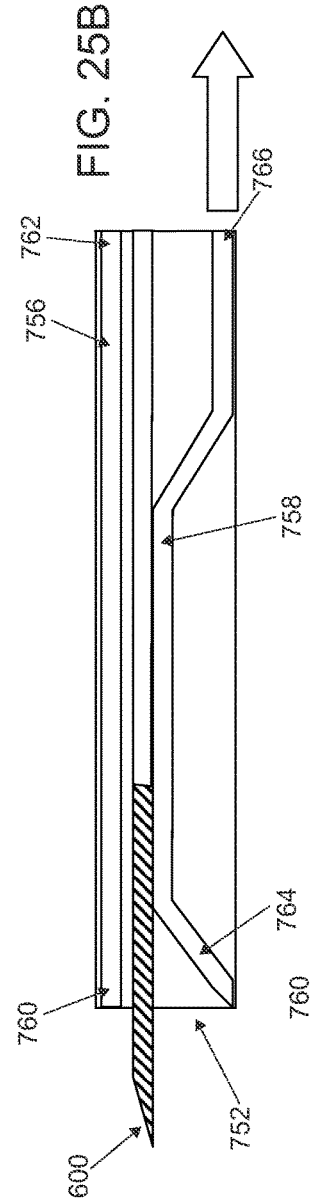
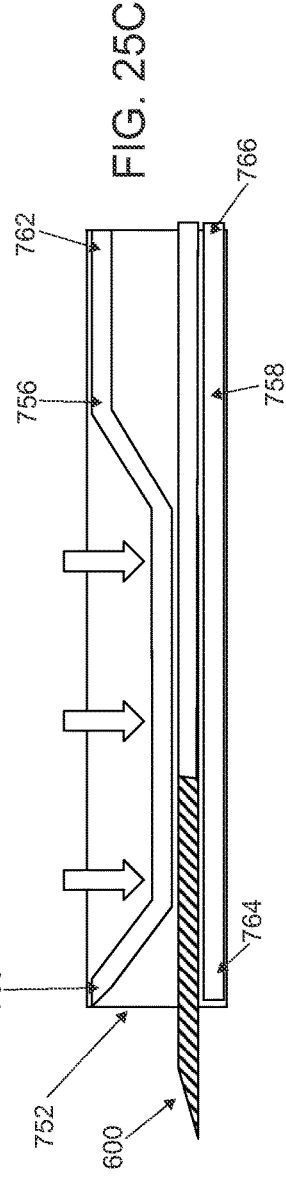

METHOD AND DEVICES FOR TREATING SPINAL STENOSIS

CROSS-REFERENCE TO RELATED APPLICATIONS

The present application is a continuation of PCT/US09/44989, filed May 22, 2009, which claims priority under 35 U.S.C. § 119(e) to U.S. Provisional Application Ser. No. 61/055,909, filed May 23, 2008, and U.S. Provisional Application Ser. No. 61/084,200, filed Jul. 28, 2008, both of which are hereby incorporated by reference in their entirety.

BACKGROUND OF THE INVENTION

Spinal stenosis is a disorder where narrowing occurs in the spaces of the spine. The disorder may affect the central canal of the spine in which the spinal cord is housed (e.g. central spinal stenosis) or the lateral foramina formed between two adjacent vertebrae from which the spinal nerves exit (e.g. lateral spinal stenosis). Spinal stenosis is frequently associated with degenerative disease of vertebral disc and/or vertebrae. The degenerative changes may cause reactive bony or ligament ingrowth and may reduce vertebral spacing, which may lead to nerve impingement. This nerve impingement may result in debilitating forms of sciatica, which is a radiating pain to limbs or upper body and further areas in the body, as well as limitations in physical movement due to this pain.

Temporary relief of pain of this condition is often sought through conservative therapy, which includes positional therapy (e.g. sitting or bending forward to reduce pressure on spine), physical therapy, and medication or drug therapy to reduce pain and inflammation. When conservative therapy fails to resolve a patient's symptoms, surgery may be considered to address the structural etiologies of the symptoms. Surgical treatments for suspected spinal stenosis often involve open procedures that require extensive dissection of muscle, connective tissue and bone along a patient's back to achieve adequate surgical exposure. These surgeries also expose the patient to a significant risk of complications, due to the presence of critical neurovascular structures near the surgical site. Specific surgical treatments include 1) foraminotomy, which involves the removal of bone surrounding an impinged nerve, 2) laminectomy, where the arch-like bone forming the posterior border of the spinal canal is removed to relieve pressure on the nerve roots or spinal cord, 3) discectomy, which involves removal of vertebral disc material impinging on a nerve, and 4) spinal fusion, which involves the use of grafts or implants to stabilize the movement between two vertebrae by eliminating any relative motion between them.

BRIEF SUMMARY OF THE INVENTION

Systems and methods for treating spinal stenosis include endoscopic access devices and spinal, stenotic tissue removal devices used to perform a foraminotomy. Some of the stenotic tissue removal devices include expandable members which may be used to control the position of the bone removal mechanism and to protect neurovascular structures and other soft tissue structures from the bone removal mechanism. Other bone removal devices include a trephine with a viewing window and a guide wire lumen used to position the trephine at a target tissue site using an anchored wire. The viewing window may be used to monitor structures or tissues adjacent to the target tissue site.

In one embodiment, a foraminotomy system is provided, comprising a cannula body with a proximal end, a distal end, an guide lumen, and an drive shaft lumen, a drive shaft in the drive shaft lumen of the cannula body, a trephine, the trephine comprising a cylindrical tube with a proximal end coupled to a distal end of the drive shaft and a distal end with a plurality of cutting members arranged along a circumferential edge of the distal end, and a guidewire with a threaded distal end configured to attached to bony tissue. The trephine may further comprise an anchor element protruding distally from the center of its distal end. In some examples, the trephine may be a rotatable trephine with a rotation axis, and may be configured with a rotation range of less than about 15 degrees, and may be coupled to a reciprocation assembly. The trephine may have a fixed position relative to the cannula body and may further comprise a handle attached to the cannula body. The cannula body may also comprise a scope lumen, and the scope lumen may comprise at least one fiber optic line, which may be located in a separate fiberoptic scope inserted into the scope lumen, or may be integrally formed with the scope lumen. The scope lumen may also comprise a distal viewing aperture, which may comprise an open or closed aperture of a side wall or end wall of the cannula body. In some examples, the closed aperture of the cannula body may comprise a transparent material or window. The rotatable trephine may be coupled to a rotatable motor. In some examples, guide lumen may be located a distance from the rotation axis of the rotatable trephine that is equal to or a greater than about the diameter of the rotatable trephine. The guide lumen may also comprise at least one or two deformable tension elements. In some examples, at least one of the deformable tension elements may user-controlled.

In another embodiment, a method of treating a patient is provided, comprising attaching a guide element to a body tissue, inserting a trephine toward the body tissue by passing a guide lumen of the trephine over the guide element, viewing a body structure adjacent the body tissue using a viewing aperture located about a distal end of the trephine, and actuating the trephine to remove at least some of the body tissue. In some examples, viewing a body structure adjacent the body tissue may comprise viewing a nerve located next to the trephine. The method may also further comprise adjusting the guide element position within the guide lumen of the trephine and/or repositioning the trephine with respect to the body tissue and the guide element by rotating the trephine about the guide element.

In one embodiment, a foraminotomy device is provided, comprising a cannula body with a proximal end, a distal end, an inflation lumen, and an drive shaft lumen, a drive shaft in the drive shaft lumen of the cannula body, a rotatable soft-tissue sparing burr coupled to a distal end of the drive shaft and located distal to the distal end of the cannula body, the rotatable soft-tissue sparing burr comprising an exposed distal tip with a roughness in the range of about 120 grit to about 200 grit, and wherein the rotatable soft-tissue sparing burr is configured with a maximum rotation speed in the range of about 5,000 rpm to about 25,000 rpm, and an inflatable balloon in communication with the eccentric inflation lumen and having a longitudinal position that overlaps with a longitudinal position of the rotatable burr.

In another embodiment, a tissue debulking system is provided, comprising a tubular body comprising a proximal end, a distal end and a longitudinal axis therebetween, a mechanical tissue debulking assembly coupled to the tubular body, an adjustment member with first adjustment surface having an adjustable separation distance from the mechanical tissue debulking assembly. The mechanical tissue debulking assembly may comprise a rotatable mechanical tissue debulking assembly, such as a rotatable burr. The adjustable separation distance is transversely oriented with respect to the longitudinal axis of the tubular body. The adjustment member may comprise an expandable member, such as an inflatable balloon. The mechanical tissue debulking assembly may be located at the distal end of the tubular body, and may optionally comprise an exposed distal end. In some embodiments, the exposed distal end may comprise a tissue debulking tip.

In some embodiments, a tissue debulking system is provided, comprising a tubular body comprising a proximal end, a distal end and a longitudinal axis therebetween, a non-oscillating rotatable mechanical tissue debulking assembly coupled to the tubular body, wherein the tissue debulking assembly comprises an abrading surface configured to abrade bone material while atraumatically deforming soft tissue contacting the abrading surface. In some further embodiments, the tissue debulking assembly is configured to abrade cortical bone material while atraumatically deforming soft tissue contacting the abrading surface. In some embodiments, the abrading surface comprises a roughness of about 50 grit to about 1000 grit, sometimes about 100 grit to about 500 grit, and other times about 120 grit to about 200 grit. In some embodiments, the abrading surface comprises a grit size of about 0.0005" to about 0.01", sometimes about 0.001" to about 0.01", and other times about 0.001" to about 0.004".

In still another embodiment, a method for treating spine disease is provided, comprising accessing a spine region of a patient, inserting a tissue debulking device into the patient, wherein the tissue debulking device comprises a mechanical tissue debulking element and an expandable positioning element, placing the tissue debulking element against a target region of the spine region, actuating the tissue debulking device, debulking tissue at the target region, expanding the expandable positioning element to exert a positioning force on the tissue debulking element. The tissue debulking element may be a rotatable burr. In some further embodiments, the method further comprises contacting the tissue debulking element with the expandable positioning element. Contacting the tissue debulking element with the expandable positioning element may occur while the tissue debulking element is actuated. The method may also further comprise resiliently deforming the expandable positioning element with the tissue debulking element.

In one embodiment, a method for treating spine disease is provided, comprising accessing a spine of a patient, forming at least one aperture along a perimeter of a bone region of the spine, inserting an expandable member into at least one aperture, and expanding the expandable member to separate the bone region from the spine. The method may sometimes further comprises endoscopically visualizing the bone region. In some embodiments, forming at least one aperture along the perimeter of the bone region of the spine may comprise forming a plurality of apertures along the perimeter of the bone region of the spine, and expanding the expandable member may comprise inflating a balloon member. In some embodiments, the bone region is located about an intervertebral foramen of the spine.

BRIEF DESCRIPTION OF THE DRAWINGS

FIG. 6 is a detailed view of one embodiment of an optional tissue transport mechanism;

FIGS. 7A to 7D depict an embodiment of a bone burr device;

FIG. 10 depicts another embodiment of a bone burr device, comprising an expandable abrasive surface;

FIG. 11A is an isometric view of another embodiment of a bone burr device;

FIG. 11B is a cross-sectional view of the bone burr device in FIG. 11A; FIG. 11C schematically depicts the bone burr device of FIG. 11A positioned in the body;

FIGS. 18A to 18E depict various configurations of a balloon component.

FIG. 19 illustrates an embodiment of a guidewire with distal threads;

FIG. 20A illustrates an embodiment of a trephine with the guidewire of FIG. 19 inserted into the guidewire lumen of the trephine; FIG. 20B illustrates the extension of the trephine head as tissue is removed;

FIGS. 21A and 21B are perspective and side elevational views of a motorized trephine device.

FIGS. 22A to 22D are schematic representations of one method for using the trephine in FIGS. 20A and 20B;

FIG. 25A depicts another embodiment of a trephine with a variable guidewire lumen; and FIGS. 25B and 25C depict one embodiment of the variable guidewire lumen.

DETAILED DESCRIPTION OF THE INVENTION

Medication and physical therapy may be considered temporary solutions for spine-related disorders. These therapies, however, may not fully address the underlying pathologies. In contrast, current surgical solutions such as laminectomy, where the laminae (thin bony plates covering the spinal canal) are removed, permit exposure and access to the nerve root which does address the underlying pathologies. From there, bone fragments impinging the nerves may be removed. Screws, interbody spacers, and fixation plates may also be used to fuse or stabilize the spine following laminectomy. These surgical techniques, however, are quite invasive and require extensive preparation and prolonged exposure time during the surgery, often prolonging an already significant recovery time. Removal of bone tissue in close proximity to nerves may also increase the risk of neurovascular damage. Other surgical methods have been attempted, such as laminotomy, which focuses on removing only certain portions or smaller segments of the laminae. Although removing less bone may be less invasive, risks of iatrogenic blood vessel and nerve damage may increase. Some spine procedures also utilize posterior approaches to the spine, which may require deliberate removal of an intervening spinous process merely to achieve access to the desired surgical site.

To be the least destructive to spine structures while preserving the strength of the bones, a spinal procedure may be minimally invasive while also reducing the amount of excised, native bone or dissection of surrounding native tissues. The exemplary embodiments described herein include but are not limited to minimally invasive access systems and methods for performing foraminotomy, and tools for removing bone while preserving the adjacent soft tissue such as nerves and blood vessels.

Figure 1:
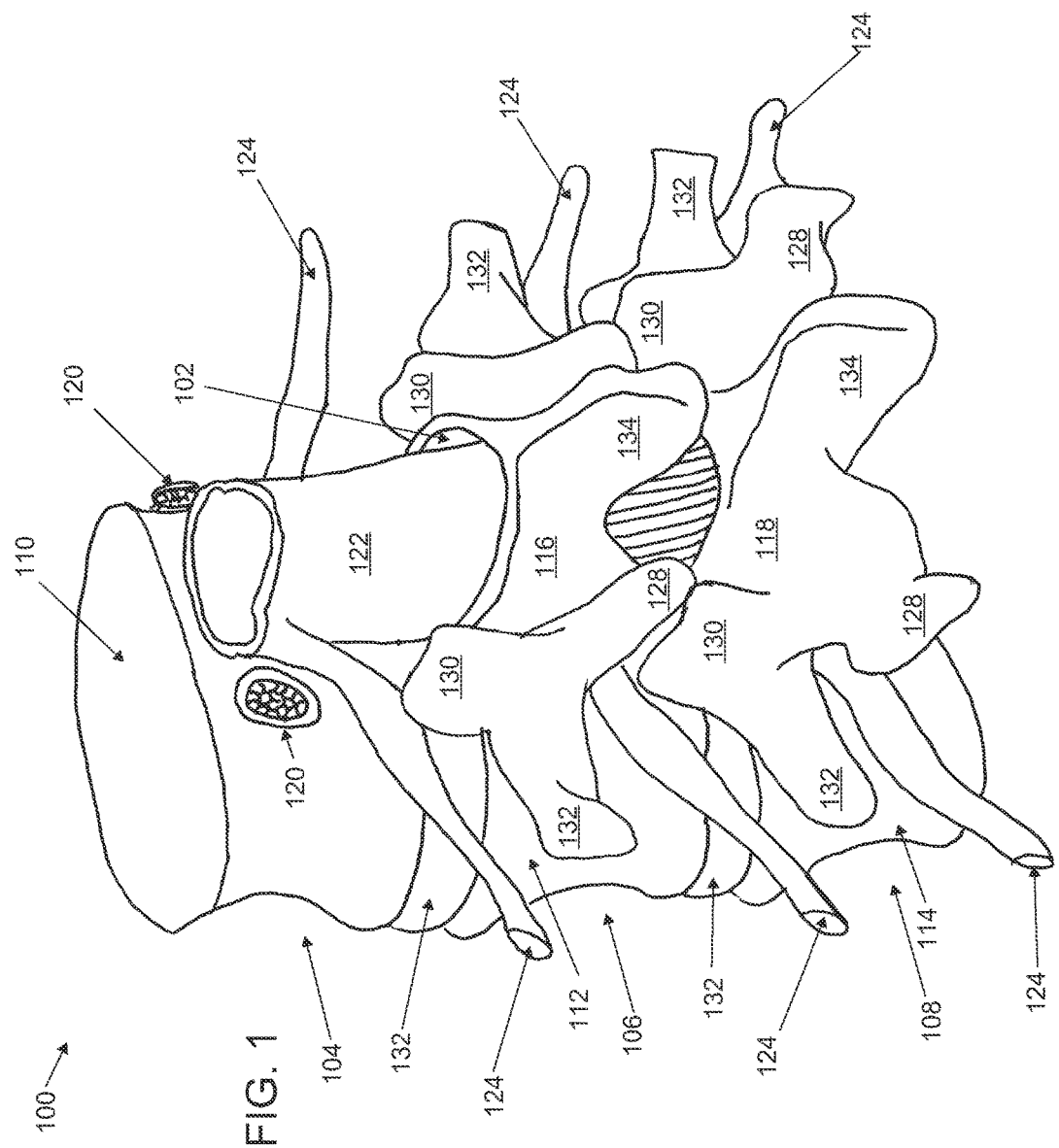
FIG. 1 is a schematic perspective view of a portion of a lumbar spine.

FIG. 1 is a schematic perspective view of a lumbar portion of a spine 100. The vertebral canal 102 is formed by a plurality of vertebrae 104, 106, and 108, which comprise vertebral bodies 110, 112, and 114 anteriorly and vertebral arches 116 and 118 posteriorly. The vertebral arch and adjacent connective tissue of the superior vertebra 104 in FIG. 1 has been omitted to better illustrate the spinal cord 122 within the vertebral canal 102. Spinal nerves 124 branch from the spinal cord 122 bilaterally and exit the vertebral canal 102 through intervertebral foramina 126 that are formed between adjacent vertebra 104, 106 and 108. The intervertebral foramina 126 are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are vertebral discs 132.

Figure 2:
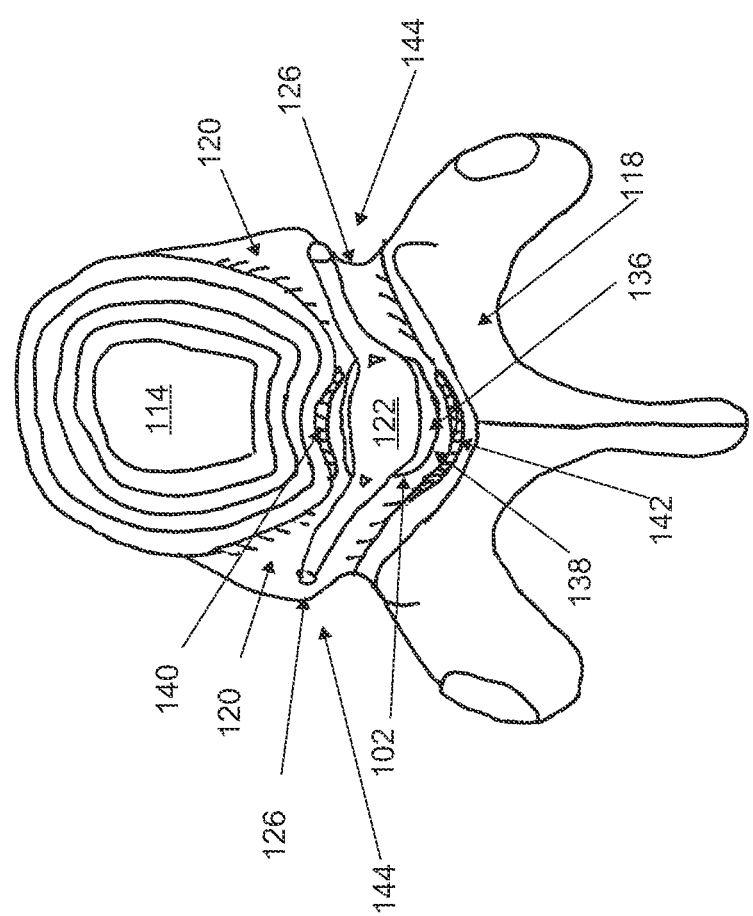
FIG. 2 is a schematic superior view of a portion of a lumbar vertebra and disc.

Referring to FIG. 2, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142, respectively, of the vertebral canal 102, and laterally by the pedicles 120 of the vertebral arches 116 and 118 and the intervertebral foramina 126. The epidural space 138 is contiguous with the paravertebral space 144 via the intervertebral foramina 126.

Figure 3A:
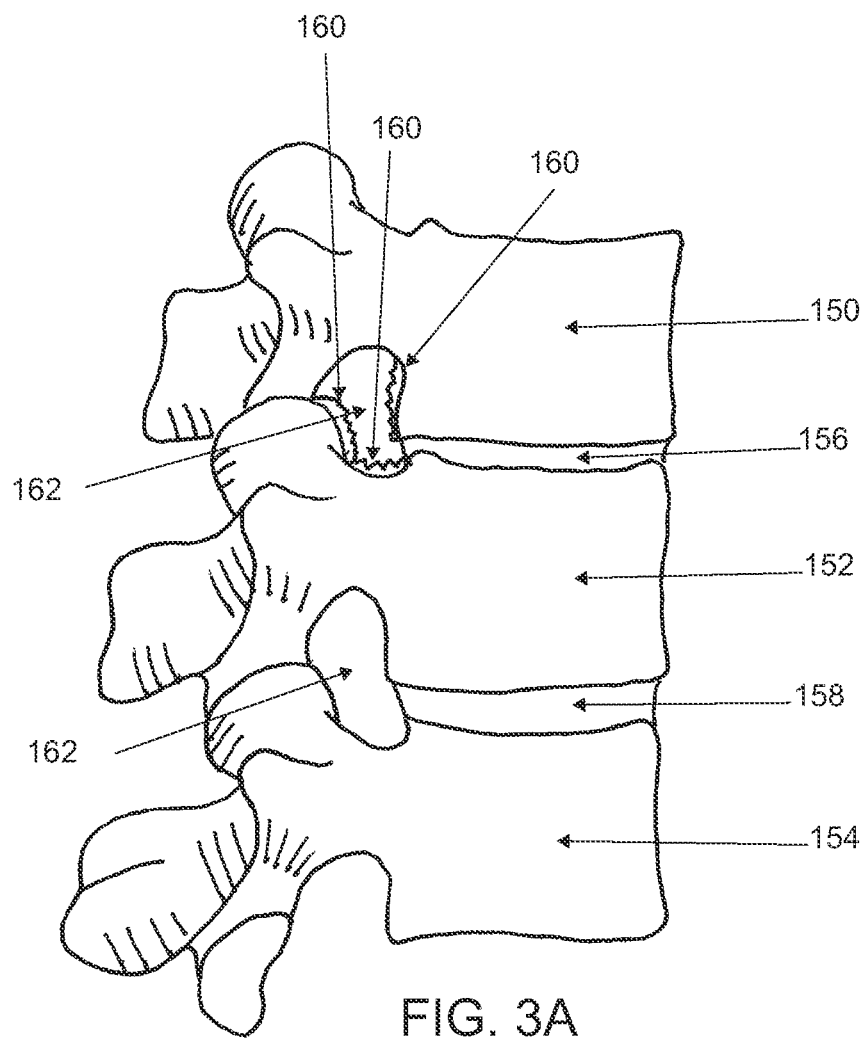
FIG. 3A is a schematic lateral view of a portion of a lumbar spine (without the spinal nerves)
Figure 3B:
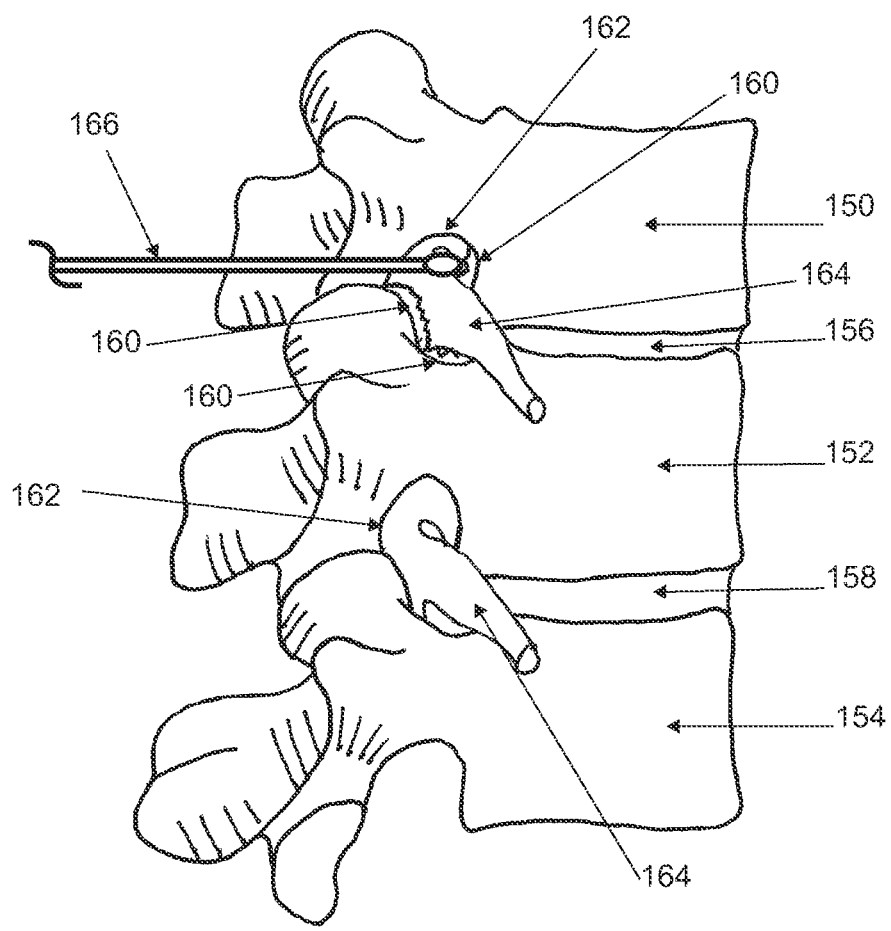
FIG. 3B depicts the portion of the lumbar spine in FIG. 3A (with the spinal nerves depicted)

With degenerative changes of the spine, which include but are not limited to disc bulging and hypertrophy of the spinal ligaments and vertebrae, the vertebral canal 102 may narrow and cause impingement of the spinal cord or the cauda equina, a bundle nerves originating at the distal portion of the spinal cord. Disc bulging or bone spurs may also affect the spinal nerves 124 as they exit the intervertebral foramina 126. FIG. 3A, for example, schematically depicts a lateral view of three vertebrae 150, 152 and 154 with intervertebral discs 156 and 158, without the spinal cord or spinal nerves. With degenerative changes, regions of bone hypertrophy 160 may develop about the intervertebral foramina 162. While secondary inflammation of the associated nerve and/ or soft tissue may benefit from conservative therapy, the underlying bone hypertrophy remains untreated. The regions of bone hypertrophy 160 may be removed, with or without other tissue, using open surgical spine procedures, limited access spine procedure, percutaneous or minimally invasive spine procedures, or combinations thereof. FIG. 3B depicts the vertebrae 150, 152 and 154 of FIG. 3A with their corresponding spinal nerves 164 during a foraminotomy procedure using a burr device 166. One example of a limited access spine procedure is disclosed in U.S. Pat. No. 7,108, 705, which is hereby incorporated by reference in its entirety. Examples of percutaneous or minimally invasive spine procedures may be found in U.S. Pat. No. 4,573,448, U.S. Pat. Nos. 6,217,509, and. 7,273,468, which are hereby incorporated by reference in their entirety.

In one particular embodiment, a patient is placed into a prone position with a pillow or other structure below the abdomen to limit lumbar lordosis. The patient is prepped and draped in the usual sterile fashion and anesthesia is achieved using general, regional or local anesthesia. Under fluoroscopic guidance, a sharp tipped guidewire, or a needle with a guidewire is inserted into the paravertebral space or epidural space from a posterior or postero-lateral location of the patient's back. In alternate embodiments, an anterior procedure through the abdominal cavity or anterior neck region may be performed. Once access to the target location is confirmed, an introducer or cannula may be inserted over the guidewire, followed by subsequent guidewire removal and insertion of an endoscope into the introducer or cannula. Alternatively, an endoscope may be inserted over the guidewire. The endoscope may be manipulated or steered to directly visualize and identify the relevant structures such as the disc, the nerve or other adjacent structures and site(s) of bone removal. In some embodiments where the patient is under local or regional anesthesia, the suspected nerve impingement may be confirmed by contacting or manipulating the suspected nerve with the endoscope, or other instrument inserted through the endoscope, and assessing the patient's response or symptoms.

Once the target region has been evaluated, any of a variety of treatments may be performed, including but not limited to the application of anti-inflammatory and analgesic agents, and the lysis of adhesions. Other treatments may include the use of a tissue removal device to remove bony tissue or hardened or calcified soft tissue to alleviate the suspected nerve or cord impingement. The tissue removal device may comprise an energy transmission device, such as a laser device manufactured by Trimedyne Inc. (Irvine, Calif.) or an ablation device produced by Arthrocare Corporation (Austin, Tex.). The tissue removal device may also comprise a mechanical device such as a rotating burr, a rongeur, a reamer, a rasp, or a curette. Examples of various tissue removal devices are disclosed in greater detail below.

Figure 4:
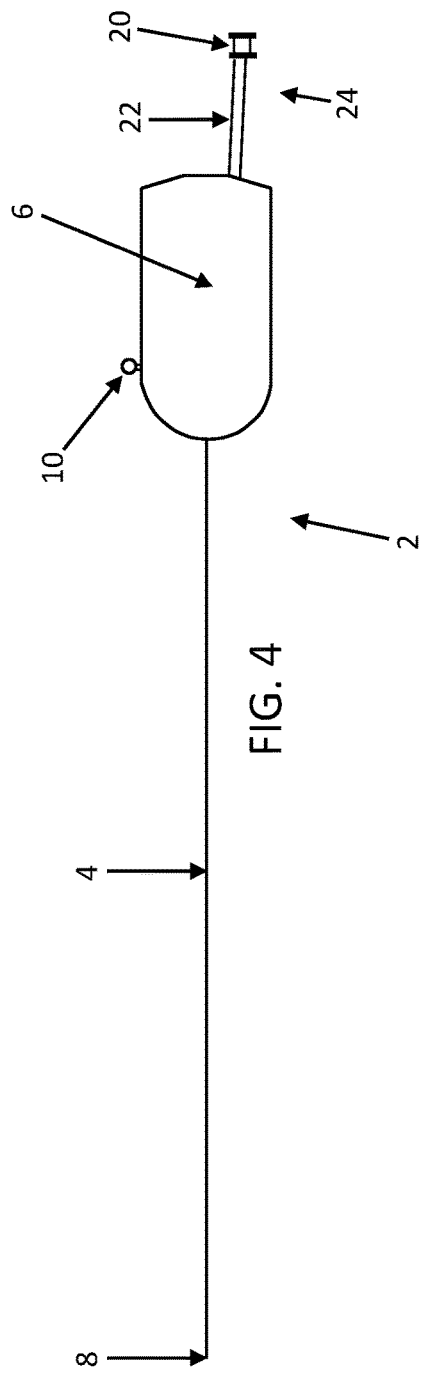
FIG. 4 is a side elevational view of an embodiment of a tissue debulking apparatus.

FIG. 4 depicts one embodiment of a tissue debulking apparatus 2, comprising an outer tube 4 coupled to a housing 6. The static outer tube 4 covers the rotating drive shaft 68 that is attached to a tissue debulking element 8. In other embodiments, the tissue debulking apparatus 2 may lack an outer tube and the drive shaft of the tissue debulking apparatus may be inserted into a lumen of a cannula or other access device. The housing 6 contains one or more components configured to control the tissue debulking element 8 and other optional features of the tissue debulking apparatus 2. The tissue debulking element 8, examples of which are described in greater detail below, may be configured to cut, chop, grind, burr, debride, debulk and/or emulsify tissue. Emulsification includes, for example, forming a suspension of tissue particles in a medium. The medium may comprise existing liquid at the target site, liquid added through the tissue debulking apparatus, and/or liquid generated by the debulking of the tissue. Optional components may include, but are not limited to, a motor configured to rotate or move the tissue debulking element, a power source or power interface, a motor controller, a tissue transport assembly, an energy delivery or cryotherapy assembly, a therapeutic agent delivery assembly, a light source, and one or more fluid seals. The optional tissue transport assembly may comprise a suction assembly and/or a mechanical aspiration assembly. One or more of these components may act through the outer tube 4 to manipulate the tissue debulking element and/or other components located distal to the housing 6, or from the housing 6 directly. In FIG. 4, for example, the tissue debulking apparatus 2 further comprises an optional port 20 that may be attached to an aspiration or suction source to facilitate transport of tissue or fluid out of the target site or patient. The suction source may be a powered vacuum pump, a wall suction outlet, or a syringe.

The housing 6 may further comprises a control interface 10 that may be used to control the power state of the tissue debulking apparatus 2, including but not limited to on and off states. The control interface 10 may comprises a lever or pivot member, but in other embodiments, control interface 10 may comprise a push button, a slide, a dial or knob, for example. In some embodiments, the control interface 10 may also adjust the motor speed and/or movement direction of the tissue debulking element 8. A bi-directional tissue debulking apparatus may be provided as a potential safety feature should the tissue debulking element 8 get lodged in a body tissue or structure. For example, the web-like connective tissue that is found in the epidural space may get wound onto or caught up on the burr device or other tissue removal device. This connective tissue may be dislodged with a bi-directional tissue debulking apparatus by reversing the direction of rotation to unwind the tissue. The control interface 10 may be analog or digital, and may comprise one or more detent positions to facilitate selection of one or more pre-selected settings. In other embodiments, a separate motor control interface may be provided for one or more features of the motor. In still other embodiments, control interfaces for other features of the tissue debulking apparatus may be provided.

Figure 5:
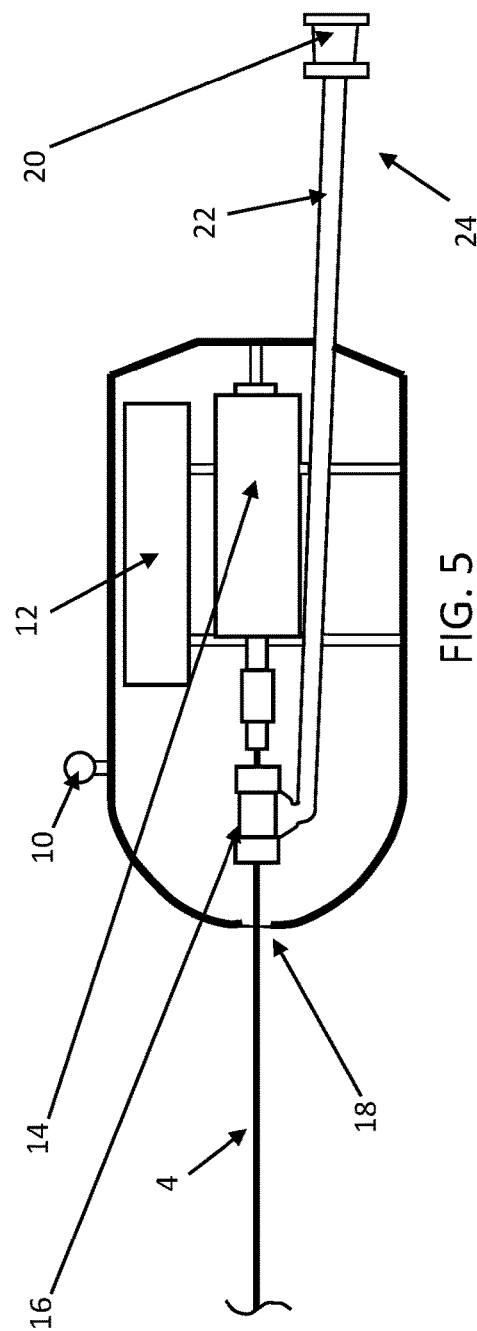
FIG. 5 is a detailed cutaway view of the apparatus in FIG. 4.

FIG. 5 depicts the tissue debulking apparatus 2 with a portion of the housing 6 removed to show various internal components. For example, the tissue debulking apparatus 2 further comprises a battery 12 to provide power to the motor 14 which drives the tissue debulking element 8. In other embodiments, a connector to an external power source may be provided in addition to, or in lieu of, the battery 12. The type of battery and power provided may differ depending upon the particular power needs of the motor and/or other components of the tissue debulking apparatus 2.

In some embodiments, the motor 14 of the tissue debulking apparatus 2 is a DC motor, but in other embodiments, the motor 14 may be configured with any of a variety of motors, including but not limited to an AC or a universal motor. The motor 14 may be a torque, brushed, brushless or coreless type of motor. In some embodiments, the motor 14 may be configured to provide a rotational speed of about 500 rpm to about 200,000 rpm, sometimes about 1,000 rpm to about 40,000 rpm, and at other times about 5,000 rpm to about 20,000 rpm. The motor 14 may act on the tissue debulking element 8 via the outer tube 4, or a by drive member located within the outer tube 4. A fluid seal 16 may be used to protect the motor 14 and/or other components of the housing 6 from any fluids or other materials that may be transported through the outer tube 4, or through the housing aperture 18. A connector or seal may also be provided about the housing aperture 18 to permit coupling of the housing 6 to a trocar, an introducer, a cannula or other tubular member into which the tissue debulking element 8 and the outer tube 4 are inserted. In some embodiments, the tissue debulking apparatus may be used with an introducer or cannula having an outer diameter of about 0.01 cm to about 1.5 cm or more, sometimes about 0.1 cm to about 1 cm, and other times about 2 mm to about 6 mm.

As shown in FIGS. 4 and 5, the tissue debulking apparatus 2 may further comprise a conduit 24 which may be used to connect the tissue debulking apparatus 2 and an aspiration or suction source. An aspiration or suction source may be used, for example, to transport fluid or material through a lumen of the outer tube 4 or through a tubular member in which outer tube 4 is inserted. In one particular embodiment, the conduit 24 comprises a port 20 which communicates with the fluid seal 16 via a length of tubing 22. The fluid seal 16 is configured to permit flow of fluid or material between the outer tube 4 and the tubing 22, while permitting movement of the outer tube 4 or a drive member therein coupled to the motor 14. In other embodiments, the conduit 24 may further comprise additional components, including but not limited to a fluid or material trap, which may be located within or attached to the housing 6, or attached to the port 20 or the tubing 22, or located anywhere else along the pathway from the tissue debulking element 8 to the suction source. In some embodiments, a separate port may be provided for infusing or injecting substances into target site using the tissue debulking apparatus 2. In other embodiments, the conduit 24 may be used for both withdrawal and infusion of materials and/or fluids, or for infusion only. Withdrawal and/or infusion may occur at the distal end of the outer tube 4, and/or through one or more openings of the tissue debulking element 8. In other embodiments, a port may be used to insert coagulation catheter, an ablation catheter or other energy delivery device to the target site.

The outer tube 4 may comprise an outer tubular member with at least one lumen, and an elongate drive member configured to mechanically couple the motor to the tissue debulking element 8. In other embodiments, the outer tube 4 may contain additional members, for example, to adjust or control the configuration of the tissue debulking element 8. In some embodiments, the outer tube 4 may comprise one or more lumens containing control wires, which may be used to manipulate the deflections of the distal end of the outer tube 4. The outer tube 4 and optional drive members may be rigid or flexible. The outer tube 4 may be pre-shaped with a linear or a non-linear configuration. In some embodiments, the outer tube 4 and the components therein may be designed to be user deformable, which may facilitate access to particular target sites, or may be steerable using a steering mechanism comprising one or more pull wires or tension elements. In some embodiments, a stiffening wire or element may be inserted into the outer tube 4 to provide additional stiffness to the tissue debulking apparatus 2. The length of the outer tube 4 between the tissue debulking element and the motor may vary from about 0 cm to about 30 cm or more in some embodiments, sometimes about 4 cm to about 20 cm, and other times about 10 cm to about 14 cm.

In other embodiments, the tissue debulking apparatus may comprise a tissue debulking element that may be detachably attachable to the shaft of a motor or coupled to a motor. In still other embodiments, the tissue debulking apparatus may comprise a tissue debulking element coupled to a shaft, wherein the shaft may be detachably attachable to a motor or a shaft coupled to a motor.

The housing 6 may be configured with a size and/or shape that permits handheld use of the tissue debulking apparatus 2. The tissue debulking apparatus 2 may comprise a grip or structure located about the outer tube 4 to facilitate handling by the user, while the proximal end of the outer tube 4 is attached to a benchtop or cart-based machine, for example, or a mounted or fixed machine. In these embodiments, the grip may or may not contain any other components of the tissue debulking apparatus, such as a motor, while the machinery at the proximal end of the outer tube 4 may contain one or more other components, for example, such as a suction system or various radiofrequency ablation components. In some embodiments, the housing 6 may have a length of about 1 cm to about 12 cm, sometimes about 2 cm to about 8 cm, and other times about 3 cm to about 5 cm. The average diameter of the housing (or other transverse dimension to the longitudinal axis of the housing) may be about 1 cm to about 6 cm or more, sometimes about 2 cm to about 3 cm, and other times about 1.5 cm to about 2.5 cm. The housing 6 may further comprise one or more ridges, recesses or sections of textured or frictional surfaces, including but not limited to styrenic block copolymers or other polymer surfaces.

As illustrated in FIG. 6, a tissue debulking apparatus may optionally comprise a tissue transport assembly 68, which may be used to facilitate transport or removal of tissue within or along the outer tube 4. In the particular embodiment depicted, the tissue transport assembly 68 comprises a helical member 70 mounted on a drive member 78 that may be rotated. Actuation of the drive member 78 may mechanically facilitate proximal movement of tissue or other materials within the channel or the lumen 72 of the outer tube 4 by rotating the helical member 70. The actuated drive member 78 will also rotate the distal burr element or other tissue debulking element 8. In some embodiments, use of the tissue transport assembly 68 may be performed at lower rotational speeds when tissue debulking is not concomitantly performed. When rotated in the opposite direction, the helical member 70 may be used expel or distally transport tissue, fluid or other materials or agents from the outer tube 4 or supplied to an infusion port of the housing 6. In some examples, the cutting edge may be provided at the opening of the outer tube 4, which may facilitate further shearing or break-up of tissue fragments or materials. The opening may also comprise beveled edge, which may or may not be at least partially sharpened. In other examples, the cutting edge may be sharpened but not beveled. Examples of tissue removal devices with beveled openings are depicted in U.S. Provisional Application Ser. No. 61/170,507, filed Apr. 17, 2009, which is hereby incorporated by reference in its entirety.

In some embodiments, the helical member 70 may have a longitudinal dimension of about 2 mm to about 10 cm or more, sometimes about 3 mm to about 6 cm, and other times about 4 mm to about 1 cm. In other embodiments, the longitudinal dimension of the helical member 70 may be characterized as a percentage of the longitudinal dimension of the outer tube 4, and may range from about 5% to about 100% of the longitudinal dimension of outer tube 4, sometimes about 10% to about 50% or more, and other times about 15% to about 25%, and still other times is about 5% to about 15%. Although the helical member 70 depicted in FIG. 6 will rotate with a tissue debulking element due to its mounting onto common structure, drive member 78, in other embodiments, the helical member 70 may also be configured to rotate separately from drive member 78. For example, the helical member 70 may comprise a helical coil located along at least a proximal portion of the lumen 72 of the outer tube 4 but is not mounted on the drive member 78. In this particular example, the helical member 70 can rotate independently of the drive member 78. In still other embodiments, the helical member 70 may be mounted on the surface of the lumen 72 and can be used to transport tissue or substances along the lumen 72 by rotation of the outer tube 4, independent of the drive member 78 or a tissue debulking element.

Although the helical member 70 is depicted as a continuous structure, in some embodiments, the helical member 70 may be interrupted at one or more locations. Also, the degree or angle of tightness of the helical member 70 may vary, from about 0.5 turns/mm to about 2 turns/mm, sometimes about 0.75 turns/mm to about 1.5 turns/mm, and other times about 1 turn/mm to about 1.3 turns/mm. The cross-sectional shape of the helical member 70 may be generally rounded as depicted in FIG. 6, but in other embodiments, may have one or more edges. The general cross-sectional shape of the helical member 70 may be circular, elliptical, triangular, trapezoidal, squared, rectangular or any other shape. The turn tightness and cross-sectional shape or area of the helical member 70 may be uniform or may vary along its length. In some embodiments, multiple the helical members 70 may be provided in parallel or serially within the outer tube 4.

In some embodiments, the drive member 78 may be configured to extend distally and retract from the outer tube 4 by a length of about 0.01 cm to about 2 cm or more, sometimes about 0.02 cm to about 1.5 cm and other times about 0.05 to about 1 cm. In some embodiments, the helical member 70 is located proximal to the tissue debulking element at a distance of about 0.01 cm to about 2 cm or more, sometimes about 0.02 cm to about 1.5 cm and other times about 0.05 to about 1 cm. In some embodiments, when drive member 78 is maximally extended from outer tube 4, helical member 70 may protrude from outer tube 4 by a longitudinal dimension of about 0.01 cm to about 2 cm or more, sometimes about 0.1 cm to about 1 cm, and other times about 0.25 cm to about 0.5 cm. In some embodiments, the degree of extension of the drive member 78 and/or the helical member 70 may affect the degree of tissue transport by the tissue transport assembly.

In some embodiments, the foraminotomy or foraminoplasty procedures may be performed without any specific protective structure or component for manipulating neural tissue away from the treatment site. In these and other embodiments, precise maneuverability may be a beneficial characteristic for performing a minimally invasive spinal surgery, to permit precise removal of smaller bone sections that are applying pressure on a nerve. In other embodiments, a protective sheath, barrier or device may be inserted between the nerve and the stenotic structure(s) to protect the nerve during bone removal. The protection device may be a separate device, or may be a component integral with the endoscope or with the bone removal tool, for example. In one example, a flexible cannula tip surrounded by a balloon is used to navigate the anatomical structure of the vertebrae and simultaneously form spacing between tissue and bone in an atraumatic manner to adjust corrective spacing and initially relieve pressure from the bone. U.S. application Ser. No. 11/373,848, which is hereby incorporated by reference in its entirety, discloses a number of embodiments for an endoscopy system comprising an atraumatic tip which may be safely used to displace sensitive or critical soft tissue structures during any of a variety of endoscopic procedures. In another example, U.S. application Ser. No. 11/362,431, which is hereby incorporated by reference in its entirety, discloses an endoscopy system comprising an extendable and steerable balloon device that may be used to manipulate tissues. Once these targeted bone areas are accessed, and nerve structure is displaced, a burr device can be inserted into a channel of the cannula and applied to cut away segments of bone. In some further embodiments, regions of bone hypertrophy or ligament calcification or hardening may be removed using a differential tissue debulking apparatus which preferentially removes certain types of materials while avoiding or reducing damage to other types of tissues. In some embodiments, the differential tissue debulking apparatus may preferentially destroy or debulk soft tissue over hard tissue, but in other embodiments, the differential tissue debulking apparatus may preferentially destroy or debulk hard tissue over soft tissue. The differential tissue debulking apparatus may be an energy transmission device or a mechanical device.

For example, the differential tissue debulking apparatus may comprise a rotatable device with a surface configuration that removes bone or other calcified or hardened tissues while generally resisting engagement or removal of softer tissues such as nerves or blood vessels. In one embodiment, the principle underlying a differential tissue debulking apparatus may be demonstrated by assessing the elastic modulus of a material.

Thus, a softer tissue will generally have a lower elastic modulus and therefore more likely to deflect away from the uneven abrading surface of the debulking apparatus rather than engage, and therefore is less likely to be abraded or damaged. The modulus of bone or hardened ligament found in spinal stenosis tissue is typically up to about 4 to about 5 orders of magnitudes higher than that of nerves and blood vessels. At a finer burr roughness, the nerves, blood vessels and other soft tissue will atraumatically deform with respect to such a debulking apparatus and not be damaged, while harder stenotic tissue will resist deformation and are impacted and damaged.

To configure a rotatable burr or cutting device, for example, to exert a particular relative tangential force, the density or spacing between the abrasive or cutting structures may be altered. In some embodiments, by increasing the density or decreasing the spacing of the tissue removal structures, the frictional or engagement force between the tissue removal element and the tissue is distributed among a greater number of structures and less concentrated. A broader distribution of force may permit soft tissues to deform in response to a rotating burr or cutting device and thereby avoid significant damage, while bone or calcified tissues are unable to substantially deform and will be abraded or removed. In some embodiments where the differential tissue removal apparatus comprises a rotatable burr, the burr may have a roughness of about 50 grit to about 1000 grit or more, sometimes in the range of about 100 grit to about 500 grit, and other times about 120 to 200. Alternatively, the roughness of the burr can be expressed in grit size as well as particle spacing. In some embodiments, grit size may be in the range of about 0.0005 inches to 0.01 inches or more, or sometimes in the range of about 0.001" to about 0.01", and other times in the range of about 0.001 inches to 0.004 inches. Also, the angle of the abrasive or cutting structures with respect to the device surface may also be configured from about 0 degrees to about 180 degrees, sometimes about 45 degrees to about 90 degrees, and other times about 70 degrees to about 90 degrees. In some embodiments, burr devices with finer grits may be used generate greater heat at the target site and may exhibit greater hemostasis function than burr devices with coarser grits.

In one embodiment, depicted in FIGS. 7A to 7D, the differential tissue removal apparatus comprises a burr element 200 with a plurality of abrasive structures 202 located on a tissue removal section 204. The burr element 200 further comprises a distal tip 206 and proximal shaft 208, but in other embodiments, the burr element 200 may comprise a distal shaft instead of a distal tip 206. The burr element 200 has a generally cylindrical shape, but in other embodiments, the burr element may be elliptical, conical, or any of a variety of other shapes. The cross-sectional shape of the burr element may be circular, ovoid, triangular, squared, rectangular or any other shape, and need not be the same along the longitudinal length of the burr element 200. As depicted in FIG. 7A, the distal tip 206 of the may have a generally convex shape, but in other embodiments, the distal tip may be generally concave, tapered, or flat, for example. The distal tip 206 may have a smooth surface, or may be covered with cutting or abrasive structures.

The abrasive structures 202, seen best in FIG. 7B, may comprise a four-sided pyramidal shape with a square base. The sides 210 and 212 of the abrasive structure 202 have a generally triangular shape with a base 214 that contacts the bases 214 of the adjacent abrasive structures 202. In other embodiments, the bases 214 of the abrasive structures 202 may be spaced apart longitudinally and/or circumferentially about 0.001 inches to about 0.06 inches, and other times about 0.006 inches to about 0.03 inches. As shown in FIGS. 7B and 7D, the angle 216 between two adjacent sides 210 of two longitudinally adjacent abrasive structures 202 is about 90 degrees, and the angle 218 between two adjacent sides 212 of two circumferentially adjacent abrasive structures 202 is about 90 degrees. In other embodiments, however, the inter-structures angles 216, 218 may be different, and may range from about 25 degrees to about 165 degrees, sometimes about 45 degrees to about 135 degrees, and other times about 65 degrees to about 100 degrees. Although the sides 210 and 212 of the abrasive structures 202 in FIG. 7B have planar configurations, in other embodiments, one or more sides may be convex, concave or other type of non-planar configuration. In some embodiments, the abrasive structures 202 may be aligned with adjacent abrasive structures or may be offset. For example, the abrasive structures 202 depicted in FIG. 7B have a pitch of about 0.012 inches, or about 200% of the longitudinal length of one abrasive structure 202. In other embodiments, the abrasive structures may have a pitch in the range of about 0.001 inches to about 0.06 inches, and other times about 0.006 inches to about 0.03 inches. Relative the longitudinal length of the abrasive structure, the abrasive structures may have a pitch in the range of about 5% to about 500% or more, sometimes about 50% to about 300%, and other times about 100% to about 200%. The abrasive structures 202 need not have a uniform size, shape, orientation or spacing.

The abrasive structures may comprise any of a variety of other shapes, including but not limited to a three-sided pyramid, a frusto-pyramidal shape, a conical or frusto-conical shape, or any other type of tapered shape. In other examples, the abrasive structures may comprise a square or rectangular block configuration, or any other type of polygonal block configuration. Alternatively, the abrasive structures may comprise one or more ridge or edge structures, which may comprise one or more curves or angles. Although the abrasive structures 202 depicted in FIG. 7B have main axes between their bases and distal tips that are generally centered about their bases, in other embodiments, the main axes may be eccentrically located. The main axes may also be perpendicular, or acutely or obtusely angled with respect to the bases. In some embodiments, the main axes of the abrasive structures may have an angle with respect to the base of the abrasive structures that is in the range of about 5 degrees to about 175 degrees, or in the range of about 45 degrees to about 135 degrees, or in the range of about 25 degrees to about 90 degrees. In some embodiments, the main axis of the abrasive structures may be characterized with respect to the direction of motion when the tissue debulking apparatus is rotated. In some embodiments, the tip or edge of the debulking structure may be characterized as having a negative, zero, or positive rake angle. In some embodiments, providing the abrasive or cutting structures with a negative rake angle (e.g. angled away from the direction of motion) may reduce the abrasive or cutting torque of the device but may increase the differential cutting characteristic of the device. In some embodiments, the device may be bi-directional and have abrasive or cutting structures configured with different rake angles in each direction, e.g. a negative rake angle in one direction and a positive rake angle in the other direction.

The length of the tissue removal section 204 of the burr element 200 may be in the range of about 0.1 inches to about 0.5 inches, examples, may be in the range of 0.2 inches to about 0.3 inches, and in still other examples, may be in the range of about 0.25 inches to about 0.75 inches. The tissue removal section 204 may have a diameter or maximum transverse width in the range of about 0.01 inches to about 0.1 inches, about 0.02 inches to about 0.08 inches, or about 0.4 inches to about 0.6 inches.

The burr element 200 may comprise any of a variety of one or more materials, including but not limited to nickel-titanium alloy, stainless steel, cobalt-chromium alloy, nickel-cobalt-chromium-molybdenum alloy, titanium-aluminum-vanadium alloy, tungsten carbide, silica carbide, diamond, and ceramic. The abrasive structures 202 may comprise the same material as the rest of the burr element 200 or may comprise a different material. In some embodiments, the abrasive structures 202 may comprise a harder material, such as diamond, glass, quartz, tungsten carbide, cobalt chromium, and ceramics.

In some embodiments, the burr element may be a solid structure without any lumens or cavities. In other embodiments, such as the burr element 250 depicted in FIG. 8, the burr element 250 may be coupled to a drive shaft 260 and comprising a channel system with at least one interior lumen 252 in communication with one or more external ports 254. In some embodiments, a burr element may have a surface configuration with various recesses and depressions. This may result in build up of debris on the surface of the burr element, which in turn may reduce the efficacy of the burr element. A burr element 250 with a fluid channel system may be cleared of accumulated surface debris by forcing pressurized fluids into the interior lumen 252 and out of the external ports 254 to flush away the debris. Fluid irrigation may be performed during and/or between actuation of the burr element 250. In some embodiments, pressurized fluid may also be forced out of the external ports 254 to push away adjacent anatomical structures or tissues, such as connective tissues or nerves, or to clean or wash away debris accumulated on the adjacent anatomical structures or tissues. In some embodiments, the external ports 254 are located on the side surface 256 of the burr element 250, but in other embodiments, one or more ports 254 may be located about the distal tip 258 of the burr element 250. Each port 254 may comprise a single opening, or a group of openings, or other type of fluid transmittable structure. Although the ports 254 may be oriented at about a 90 degree angle to the side surface 256 and/or interior lumen 252, in other embodiments, other angular orientations may be used. For example, in some embodiments, one or more apertures may be oriented at an angle in the range of about 5 degrees to about 175 degrees with respect to the side surface, interior lumen or the surface of the distal tip.

Figure 8:
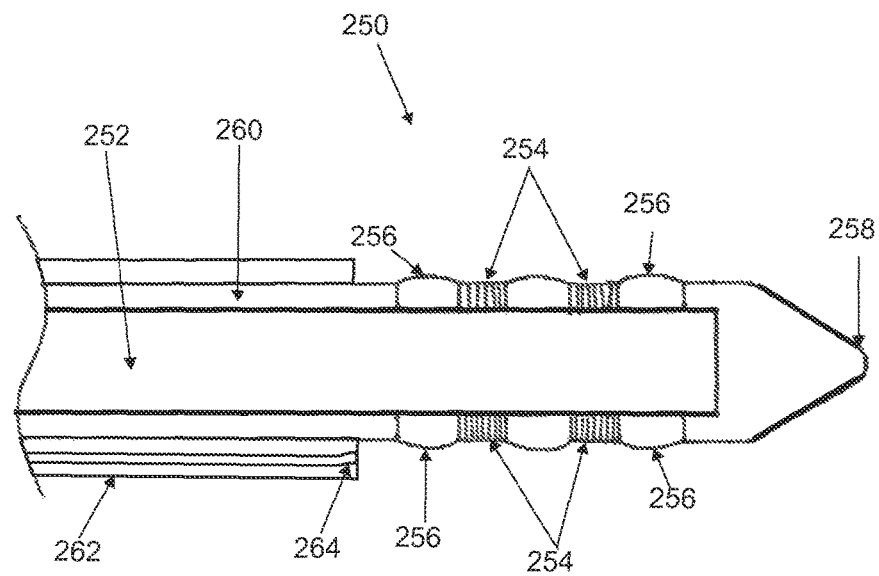
FIG. 8 depicts another embodiment of a bone burr device.

In some embodiments, in addition to or in lieu of using the ports 254 for flushing out fluid, the ports 254 may also be used to aspirate or vacuum fluid and suspended material out of the treatment site. In other embodiments, the outer tube 262 in which the drive shaft 260 resides may optionally comprise one or more ports 264 which may be used to infuse and/or aspirate fluid. As depicted in FIG. 8, the ports 264 may be angled such that the fluid flow path out of the ports 264 is directed across the surface of the burr element 250. In some embodiments, the ports 264 may comprise an orientation angle in the range of about 0 degrees to about 90 degrees with respect to the burr element 250 and the outer tube 262, while in other embodiments, the ports 264 may have an orientation angle in the range of about 0 degrees to about 45 degrees, and sometimes in the range of about 5 degrees to about 15 degrees. The sizes and configurations of the ports 264 need not be the same.

Figure 9:
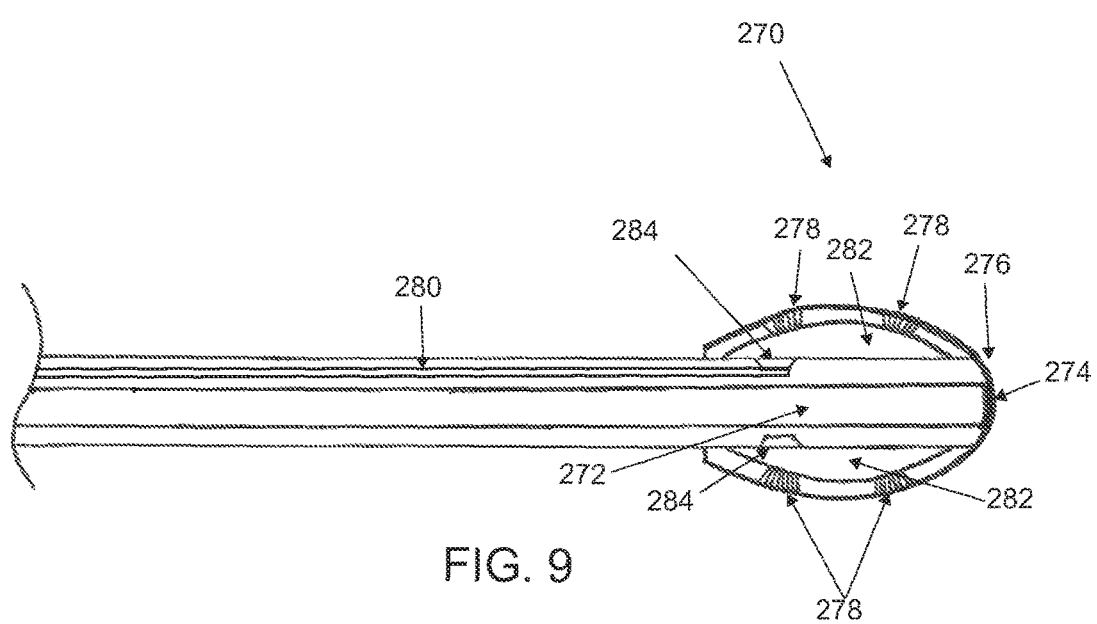
FIG. 9 depicts another embodiment of a bone burr device.

In other embodiments, depicted in FIG. 9, the burr element 270 may comprise a longitudinal lumen 272 with a distal opening 274 at the distal tip 276 of the burr element 270. The longitudinal lumen 272 may be used, for example, to insert an endoscope to visualize the target area, a manipulation member to push away structures from the burr element 270, or an anchoring member to maintain the position of the burr element 270 during use. In some embodiments, an endoscope may be used to visualize the bone and nerve, and/or to gauge the cutting depth. In some embodiments, the manipulation member may comprise rigid or steerable wire with an atraumatic tip. The anchoring member may also comprise a rigid or steerable wire with an atraumatic tip, but in some embodiments, may comprise a penetrating or piercing tip. In some embodiments, one or more separate internal lumens 280 may be provided for the radial ports 276. For example, the burr element 270 may be configured as in FIG. 9 such that an internal lumen 280 is in fluid communication with a burr cavity 282 of the burr element 270 using one or more internal ports 284. Fluid may then stream or flow out of the burr cavity 282 through the radial ports 278.

In other embodiments, the longitudinal lumen may be in communication with one or more radial ports of the burr element to permit infusion of fluid through one or more radial ports. In some further embodiments, fluid infusion may occur even while an instrument resides within the longitudinal lumen. For example, the longitudinal lumen may be configured with an enlarged cross-sectional area and/or a cross-sectional shape different than the instrument. In some embodiments, the instrument, such as the endoscope or the manipulation member, may be configured to selectively occlude one or more radial ports and/or the distal opening of the longitudinal lumen by either rotation and/or axial displacement of the instrument within the longitudinal lumen. The configuration may comprise one or more open channels, grooves or recesses on the outer surface of the instrument which permit the passage of fluid when positioned in alignment with the radial ports and/or the distal opening. In still other embodiments, radial ports are not provided on the burr element and fluid irrigation may occur only through the distal opening of the longitudinal lumen.

In another embodiment, the tissue debulking apparatus comprises a plurality of abrasive or cutting structures located on an expandable surface, such as an inflatable balloon. Referring to FIG. 10, the tissue debulking apparatus may comprise an expandable abrasive balloon 300 mounted on a rotatable drive shaft 302. A plurality of cutting or abrasive members 304 are located on the balloon surface 306, along with one or more flush ports 308. Although the abrasive members 304 and the flush ports 308 in FIG. 10 are provided in an alternating arrangement, in other embodiments, the arrangement or spacing of the members 304 and the ports 308 may be different. The expandable balloon 300 may be configured such that the balloon 300 in the uninflated state lies against the support shaft 302, but upon infusion of fluid from the shaft ports 310 into the balloon cavity 312, the balloon 300 expands outward. The degree of expansion may depend upon one or more factors, including but not limited to the rate of fluid infusion and the opening pressure and/or flow resistance of the flush ports 306, if any. As the balloon 300 expands, fluid may also flush out of the flush ports 308. In some embodiments, one or more flush ports 306 are configured to be always open but the plurality of flush ports 306 providing sufficient resistance to permit fluid pressure build up within the balloon cavity 302 at certain fluid infusion rates. In other embodiments, the flush ports 306 may comprise slits or flaps which are configured to remain closed until a certain balloon cavity pressure is achieved. The configuration of the flush ports 306 need not be the same and in some embodiments, selective use of the flush ports 306 may be performed by adjusting the infusion fluid pressure to adjust the number of open flush ports 306. In an alternate embodiment, a plurality of balloons may be provided on a support shaft and separate flush ports may be provided on the rotatable drive shaft, between the individual balloon surfaces and directed to the balloon surfaces.

The balloon may comprise any of a variety of materials, including but not limited to silicone, polyurethane, copolymers of polyurethane and silicone, natural rubber, synthetic rubber, nylon, natural and synthetic rubbers, polyethylene, polyethylene terephthalate, polyethylene terephthalate and other polyesters, polyisoprene, polyisobutylene, nylon and other polyamides, polyesters, olefins, PVC and other elastoplastics. In some embodiments, the balloon material may comprise an extruded material, with or without heat treatment to alter the expansion characteristics of the balloon 300. In one example, the extruded polymer material may be heat treated while in an expanded state to re-orient at least some of the longitudinally oriented polymer chain toward a circumferential orientation. The balloon material may be attached to the support shaft 302 by heat bonding, adhesives, mechanical attachment mechanisms such as crimp rings, or combinations thereof. The abrasive structures or particles 308 may be embedded onto the balloon 300 using heat treatment, for example, while the balloon 300 is in either the expanded and/or deflated states.

In some embodiments, the abrasive balloon 300 may be inserted between a bony surface and a nerve in the uninflated state. The abrasive balloon 300 may be actuated first to remove material from the bony surface and subsequently inflated, or the balloon 300 may be expanded first separate the nerve from the bony surface, followed by subsequent actuation of the balloon 300. In some instances, the expansion of the balloon 300 may alter the abrasive characteristics of the balloon, for example, by increasing the spacing or separation of the cutting or abrasive particles 308 on the balloon 300. In other instances, balloon expansion may be used to exert a greater tissue debulking force against the target structure. Thus, the balloon may be used to control the cutting or abrasive force applied to the bone by incremental inflation to achieve a desirable amount of pressure. This pressure may be used to adjust the abrading rate of the apparatus against the bone, which may provide greater precision and safety when used near critical structures such as the spinal nerve.

In another embodiment, depicted in FIGS. 11A and 11B, the tissue debulking apparatus 330 comprises a multi-lumen shaft 332 with a burr component 334 and a balloon component 336 provided in separate channels 338 and 340 of the shaft 332. In this particular embodiment, each component 334 and 336 contains their own channel 338 and 340 and are independently movable longitudinally for individual depth control and angular orientation. In other embodiments, the tissue debulking apparatus may be configured so that the burr component and the balloon component have fixed positions and orientations with respect to the multi-lumen shaft. In some embodiments, the size of the balloon component 336 in either the unexpanded or expanded state is larger than the size of the burr component 334. In some embodiments, a larger balloon component 336 may provide greater protection for adjacent anatomical structures from inadvertent damage from the burr component 334.

In use, the balloon component 336 may be used to protect one or more tissues or structures from the burr component 334, and thus may act as a protective cushion for the nerve while the burr component 334 is actuated. In some embodiments, the balloon component 336 may also be used to move the position of the burr component 334 and/or to alter the force exerted by the burr component 334 onto the target tissue or structure. Here, the burr component 334 may be placed against the bone and actuated to remove the bone, while the balloon component 336 is inflated so that the burr component 334 is pushed further into the bone and is able to remove a larger portion of the bone using a minimally invasive approach. This permits deeper removal of material, while torqueing of the balloon component 336 with respect to the burr component 334 permits directional changes to the grinding or abrading to widen the range of tissue removal. In alternate embodiments, the burr component 334 may be in a retracted position relative to the multi-lumen shaft 332 as the uninflated balloon component 336 is advanced into position and inflated. The balloon component 336 may be used to anchor the distal end of the tissue debulking apparatus 330 as the burr component 334 is actuated and advanced toward the material to be removed.

Figure 17A:
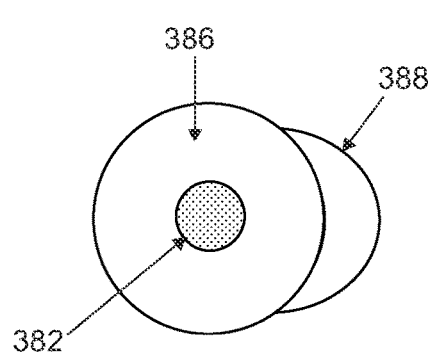
FIGS. 17A and 17B are front and side elevational views, respectively, of another embodiment of a tissue debulking apparatus.
Figure 17B:
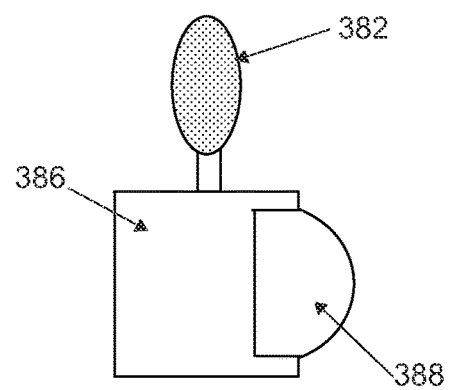

In an alternate embodiment, depicted in FIGS. 17A and 17B, the burr component 334 of the tissue debulking apparatus 330 may be used to form one or more openings or holes 400 may be formed about the unexposed perimeter of the bone to be removed. The holes 400 may be formed using a separate catheter or cannula-based drill, or a burr device as described herein, and the holes need not have a uniform shape or size. For example, one or more larger holes 402 may be formed generally about the middle region 404 of the targeted bone area 406 may be formed. A deflated balloon component 336 of the tissue debulking apparatus 330 (or a separate balloon instrument) may then be used and inflated to crack or separate the targeted bone area 406 along through all the multiple holes 400 and 406, creating fragments 408 and relieving the compression on the associated nerves or vessels.

Although the embodiments described herein may by used to perform foraminotomy procedures, the embodiments may also be used or adapted for use to remove bone or calcified tissues from other parts of the body. In other embodiments, the burr components may be further tuned to differentiate between more elastic soft tissues (e.g. vasculature and neural tissue) and firmer or calcified soft tissues (e.g. ligaments and tendons). For example, in some embodiments, the tissue debulking apparatus may be inserted into the epidural space and may be used to treat central spinal stenosis. Treatment of central spinal stenosis may involve of bone of the overlying lamina and/or soft tissue within the central spinal canal, such as a thickened or calcified longitudinal ligament or the ligamentum flavum.

Figure 12A:
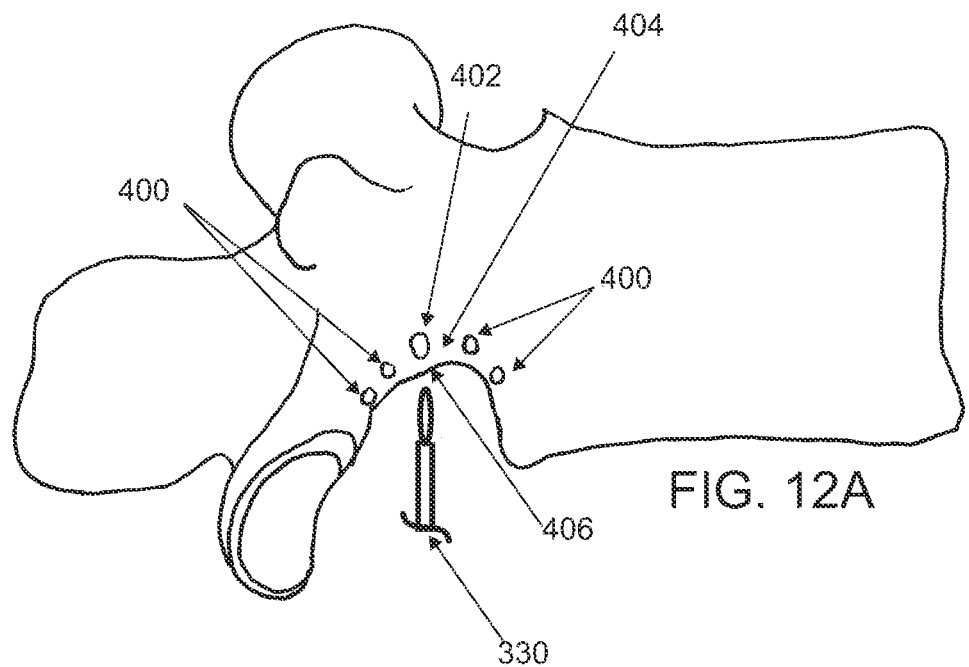
FIGS. 12A and 12B schematically depict one embodiment for treating spinal stenosis.
Figure 12B:
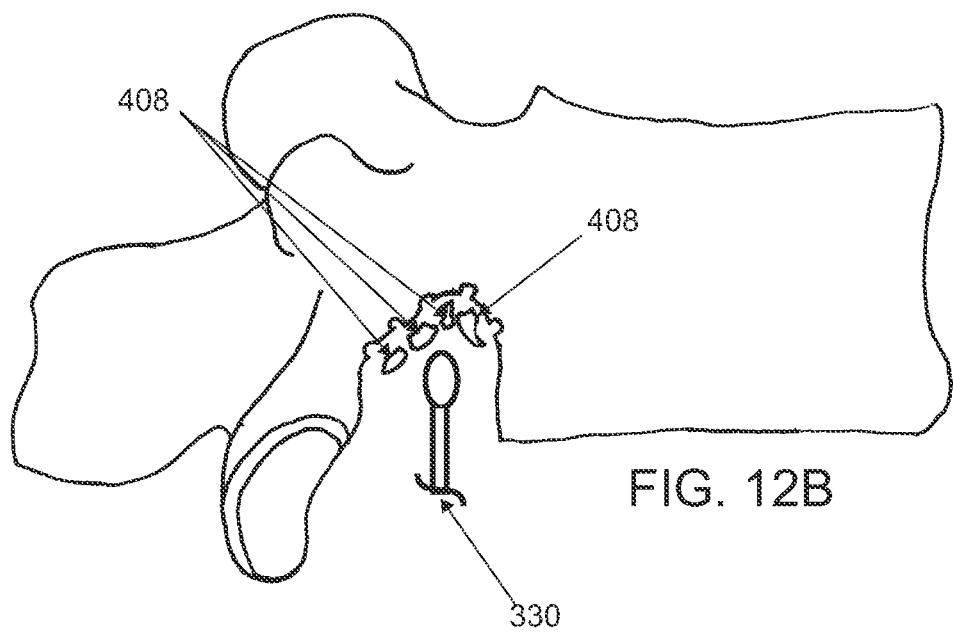
Figure 13A:
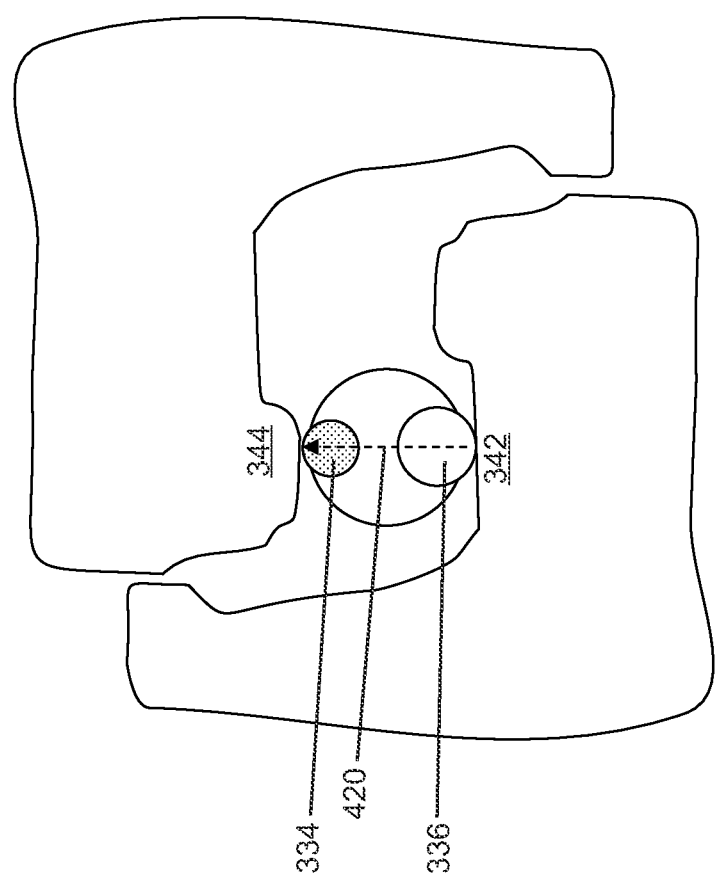
FIGS. 13A to 13C schematically illustrate exemplary uses of the tissue debulking apparatus of FIG. 11A.
Figure 13B:
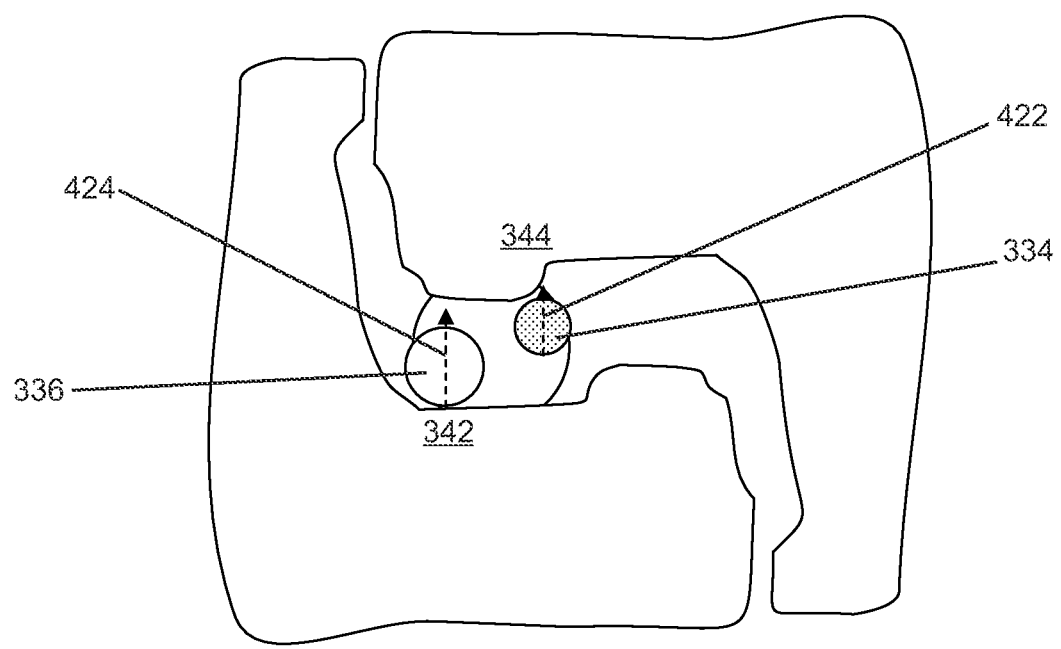
Figure 13C:
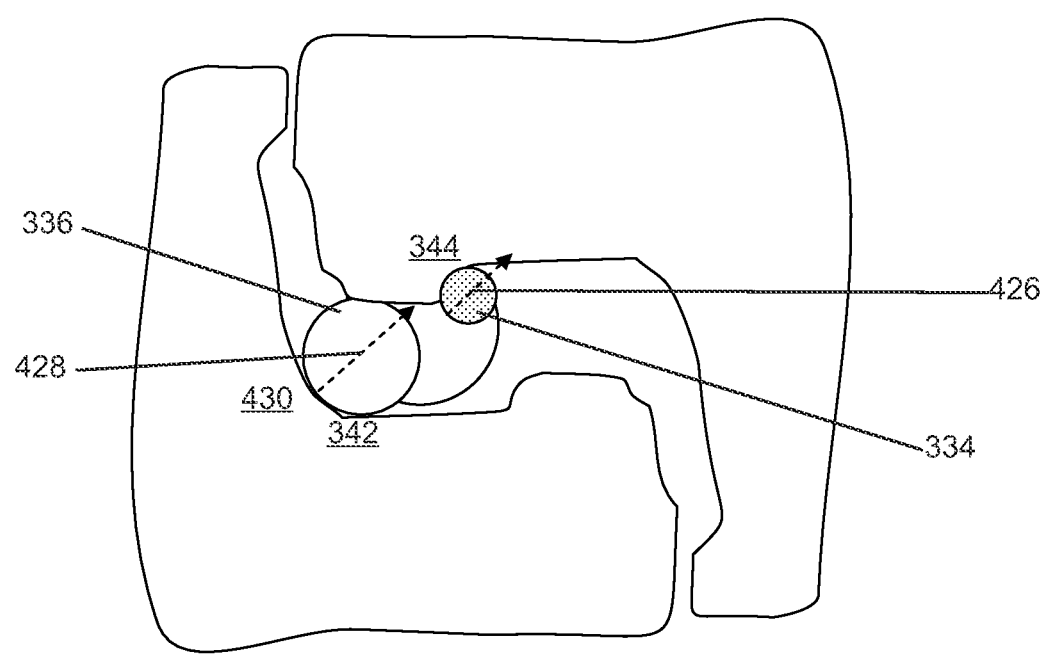

Referring to FIG. 11C, the balloon component 336 may be inserted or wedged between the burr component 334 and a base structure 342 (e.g. nerve and/or bone) opposite the target site 344 (e.g. bone). As the bone is removed by the burr component 334, the operator manipulates the tissue debulking apparatus 330 by rotating the multi-lumen shaft 332 and/or inflating the balloon component 336. By inflating the balloon component 336 against a base structure 342, the balloon component 336 provides a counter-force at the distal end 346 of the shaft 332 to move the burr component 334 in a direction away from the leveraging structure 342. In contrast, direct angulation or manipulation of the multi-lumen shaft 332 may involve leveraging the shaft 332 at an intermediate position 348 along the shaft 332 adjacent the percutaneous skin site, which may be less precise and therefore may be less safe. The direction of displacement is generally determined by the orientation of the balloon component 336 with respect to any adjacent structures. In some embodiments, the leveraging structure 342, the balloon component 336 and the burr component 334 may generally be aligned on a single movement axis (e.g., FIG. 12A), but in other embodiments, the burr component 334 may have a different movement axis (e.g., FIG. 12B). In still other embodiments, the net direction of movement may change as the balloon component 336 is inflated, due to contact with additional leveraging structures as the balloon component 336 is expanded towards its upper range (e.g., FIG. 12C).

Figure 14A:
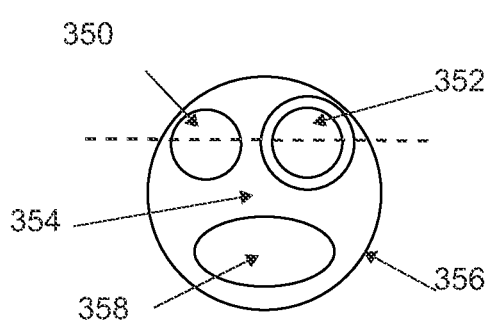
FIG. 14A is a front elevational view of another embodiment of a tissue debulking apparatus with an additional instrument lumen.
Figure 14B:
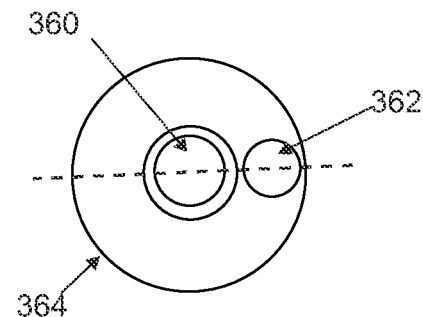
FIG. 14B is a front elevational view of another embodiment of a tissue debulking apparatus with a centrally located expandable member.

Referring back to FIG. 11B, the two channels or lumens 338 and 340 may be aligned along a line through the center 354 of the shaft 332, which may facilitate the relative directional placement of the balloon component 336 when rotating the shaft 332. In another embodiment depicted in FIG. 14A, the burr component 350 and the balloon component 352 are both located eccentrically with respect to the central longitudinal axis 354 of the multi-lumen shaft 356 but not in alignment that passes through the central longitudinal axis 354. In this particular embodiment, an additional lumen 358 may be provided for additional instrumentation. In still other embodiments, one or more components may be located centrally. In FIG. 14B, for example, the balloon component 360 is centrally located while only the burr component 362 is eccentrically located with respect to the shaft 364.

Figure 15A:
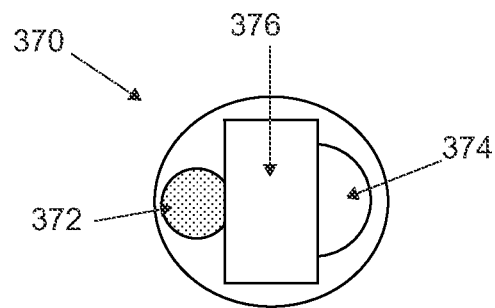
FIGS. 15A and 15B are front and side elevational views, respectively, of another embodiment of a tissue debulking apparatus.
Figure 15B:
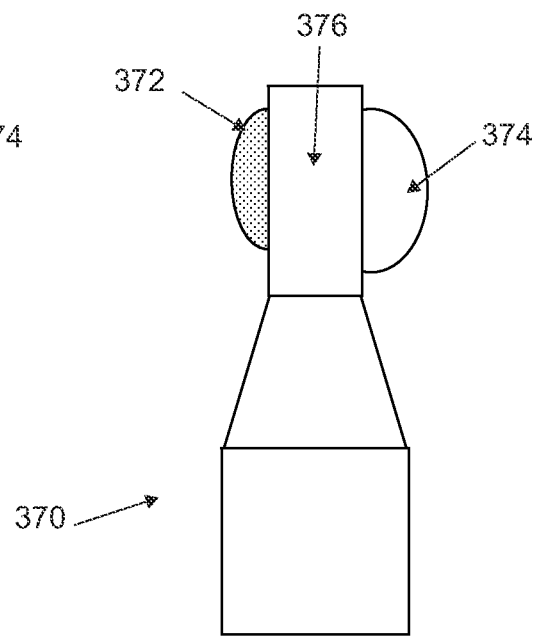
Figure 16A:
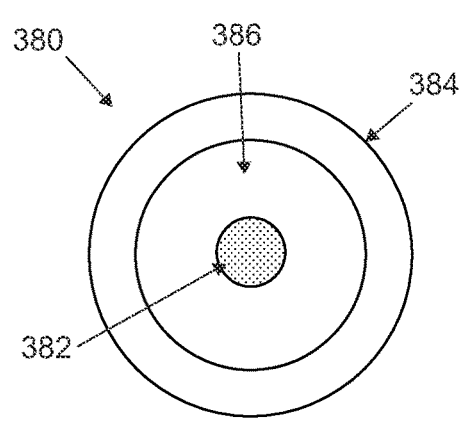
FIGS. 16A and 16B are front and side elevational views, respectively, of still another embodiment of a tissue debulking apparatus.
Figure 16B:
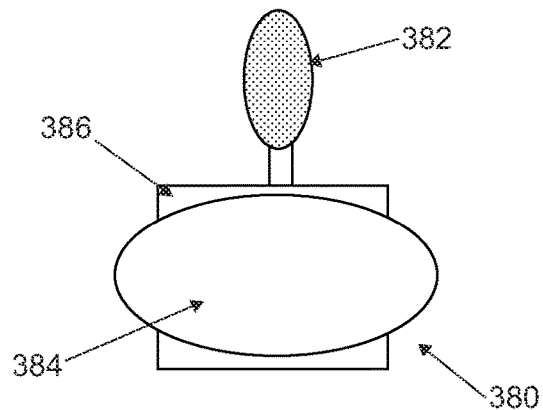

In one alternate embodiment depicted in FIGS. 15A and 15B, the tissue debulking apparatus 370 comprises a distally located burr component 372 and a distally located balloon component 374 separated by a fixed hood or barrier 376. In some embodiments, one or both of the components 372 and 374 may be at least partially mounted or coupled to the fixed barrier 376. In still another alternate embodiment illustrated in FIGS. 16A and 16B, the tissue debulking apparatus 380 comprises a distally located burr component 382 and one or more proximally located balloon components 384. The proximally located balloon 384 may have a complete circumferential configuration as shown in FIGS. 16A and 16B, or may comprise a balloon 388 with a partial circumferential configuration as shown in an alternate embodiment depicted in FIGS. 17A and 17B.

Referring back to FIG. 11A, the burr component 334 of a tissue debulking apparatus 330 may have a differential tissue debulking burr configuration, which may be configured not only to differentiate soft tissue from bone, but may also be configured to resist damage against the balloon component 336. Alternatively, the balloon component 336 may be configured such that its material and/or shape provide resistance to damage from the differential tissue debulking burr configuration. For example, the balloon component 336 may be configured to deformably expand into contact with an actuated burr component 334 without significant tearing or puncturing of the balloon component 336. In other examples, a pressure restrictor may be provided to limit the pressurization force acting on the balloon component 336 when inflated. In some instances, excessive inflation pressures result in contact of the balloon component 336 with the burr component 334, and/or cause the balloon component 336 to assume a rigid configuration which may be damaged by some differential tissue debulking burr configurations. In some embodiments, the pressure restrictor may limit the pressurization of the balloon component 336 to no greater than about 40 psi, but in other embodiments, the pressure restrictor may be set to a pressure limit of no greater than about 30 psi, or sometimes no greater than about 25 psi or no greater than about 15 psi.

The balloon component 336 may comprise a symmetric, elliptical-shaped burr that is centrically mounted on a balloon shaft 342. In other embodiments, however, the balloon component may be configured with any of a variety of shapes, including but not limited to a toroidal balloon, a conical or frusto-conical balloon 500 (e.g., FIG. 18A), a box-like balloon 502 (e.g., FIG. 18B), or a semi-cylindrical balloon 504 (e.g., FIG. 18C), or a hemi-tubular balloons 506 and 508 (e.g., FIGS. 18D and 18E), for example. In some embodiments, the hemi-tubular balloons 506 and 508 may have an angular orientation such that their concave surfaces 510 and 512, respectively, are facing the burr components of their respective tissue debulking apparatuses. As shown in FIGS. 18A and 18E, the balloon components 500 and 508 need not have a generally uniform cross-sectional shape or size along their longitudinal lengths. In some embodiments, to achieve certain expanded shapes, the balloon may comprise a generally flexible but non-elastic material. Balloons comprising non-elastic materials may utilize vacuum or suction sources to collapse the balloon into its unexpanded configuration. In some further embodiments, non-elastic balloons may be configured with changes in material thickness to facilitate folding or pleating of the balloon when collapsed to reduce the risk that wrinkles or other surface irregularities in the unexpanded configuration may affect delivery or withdrawal of the balloon component.

FIG. 19 depicts another embodiment of a foraminotomy system, comprising a sharpened guidewire 600 that may be anchored into bony or calcified tissue. The guidewire 600 comprises a sharpened distal tip 602 and a region of helical threads 604 that may be used to further penetrate any bony tissue. In other embodiments, an expandable, coiling, barbed, or ribbed configuration may be provided for insertion into soft tissues or bony tissues. The distal tip 602 may have any of a variety of configurations, including but not limited to a conical or a beveled configuration, for example. The guidewire 600 be rigid or flexible, and its rigidity or flexibility may vary along its length. The guidewire 600 may be placed at the target site by any of a variety of procedures, including surgical, limited access and minimally invasive access procedures. For example, the guidewire 600 may be placed using any of a variety of spinal endoscopy systems, including those having working lumens in addition to direct optical visualization systems. The length of the guidewire may be in the range of about 3 inches to about 6 feet or more, sometimes about 6 inches to about 3 feet, and other times about 8 inches to about 18 inches. The diameter of the guidewire may be in a range similar to standard guidewires or Kirschner wires.

Referring to FIG. 20A, once the guidewire 600 has been positioned at the desired target tissue site, an elongate trephine device 610 with a guidewire lumen 612 may be passed over the guidewire 600 toward the target site. The trephine device 610 may comprise a cutting assembly 614 with a circular configuration. In this particular embodiment, the cutting assembly 614 comprises a plurality of cutting teeth 616. Although the cutting teeth 616 in FIG. 20A are depicted as having a triangular shape, and of a variety of cutting teeth configurations may be used. The cutting teeth may be squared or rounded, for example, and the cutting teeth may be generally symmetrical about their midlines or may be offset. Thus, the cutting teeth may be configured to cut in generally one direction or in two directions. The cutting teeth 616 may also be positioned in a perpendicular orientation with respect to the distal surface 618 of the trephine device 610, but one or more teeth may also be angled radially inward or outward. In this particular embodiment, the cutting assembly 614 has a perimeter that lies within the perimeter of the distal surface 618 of the trephine device 610, but in other embodiments, the perimeters of the cutting assembly and the trephine device may be similar or equal in size and shape. The cutting teeth 616 may comprise materials such as stainless steel (including but not limited to cold-worked 304/416 stainless steel, full hard 17-4 stainless steel, and 400 series stainless steel), Ti6Al4V, cobalt chromium, tungsten carbide, diamond or ceramic for example, and may be coated with titanium nitride, chrome or other materials to further harden the edges or tips. The materials comprising the cutting teeth 616 may be the same or may be different from materials comprising the rest of the cutting assembly 614. In some embodiments, the shaft 622 of the trephine device and the rest of the cutting assembly 614 may comprise clear materials to facilitate forward viewing of the tissues and may comprise materials such as glass, quartz, diamond, or transparent polymers such as nylon-12, polycarbonate, acrylic or polyester, for example.

Referring still to FIG. 20A, the trephine device 610 further comprises a viewing aperture 620, which is in communication with a scope lumen located within the shaft 622 of the trephine device 610. The viewing aperture 620 permits the viewing of the tissues and structures adjacent the cutting assembly, such as the spinal nerve being impinged by the structures at the target tissue site. The viewing apertures may be open apertures or may be covered apertures. A covered aperture may be covered with an optically clear material such as glass, nylon-12, PEBAX, PET, FEP, PTFE, polyolefin, acrylic, polycarbonate or polyethylene, for example. The viewing aperture 620 in FIG. 20A is located on the side surface 624 of the outer shaft 622, but in some embodiments, a viewing aperture may be provided on the distal surface 618. In some embodiments, multiple viewing apertures may be provided about the distal end of the trephine device 610, as well as at more proximal locations. In some further embodiments, one or more viewing apertures may span both the distal surface and the side surface of the shaft. The side surface 624 of the shaft may be smooth or polished, which may reduce the risk of snagging adjacent tissues and structures. The outer shaft 622 may comprise any of a variety of rigid or flexible materials, and in some embodiments, may comprise a tube of clear material.

As the cutting assembly 614 removes tissue, the shaft 622 of the trephine device 610 may or may not be able to pass farther down the guide wire 600, depending the remaining tissue. Referring to FIG. 20B, the cutting assembly 614 is provided on an extendable drive shaft 626 which can continue to rotate or reciprocate to cut away tissue as it is extended. FIG. 20B also depicts the cylindrical outer shape of the base 628 of the cutting assembly 614. In some embodiments, the base may comprise a solid cylinder, but in other embodiments, base 628 may have a tubular configuration with an open anterior face and an internal cavity of lumen. In some instances, the open face and internal cavity may permit the trephine to remove a bone or tissue core, which may be retained by the cavity and withdrawn from the body with the trephine. In other embodiments, the trephine may break up tissue or bone, which is then suctioned away by an optional suction lumen of the trephine, or another instrument.

The actuation of the cutting assembly 614 may be manually performed by turning a handle or lever located at the proximal end of the trephine device 610, but the actuation may also be motorized. The motor drive assembly attached to the drive shaft 626 may be configured with a rotary action or a reciprocating action. In some embodiments, the rotation or oscillations may be in the range of about 200 rpm/Hz to about 20,000 rpm/Hz or higher, sometimes about 1,000 rpm/Hz to about 12,000 rpm/Hz, and other times about 5,000 rpm/Hz to about 10,000 rpm/Hz.

Figure 21C:
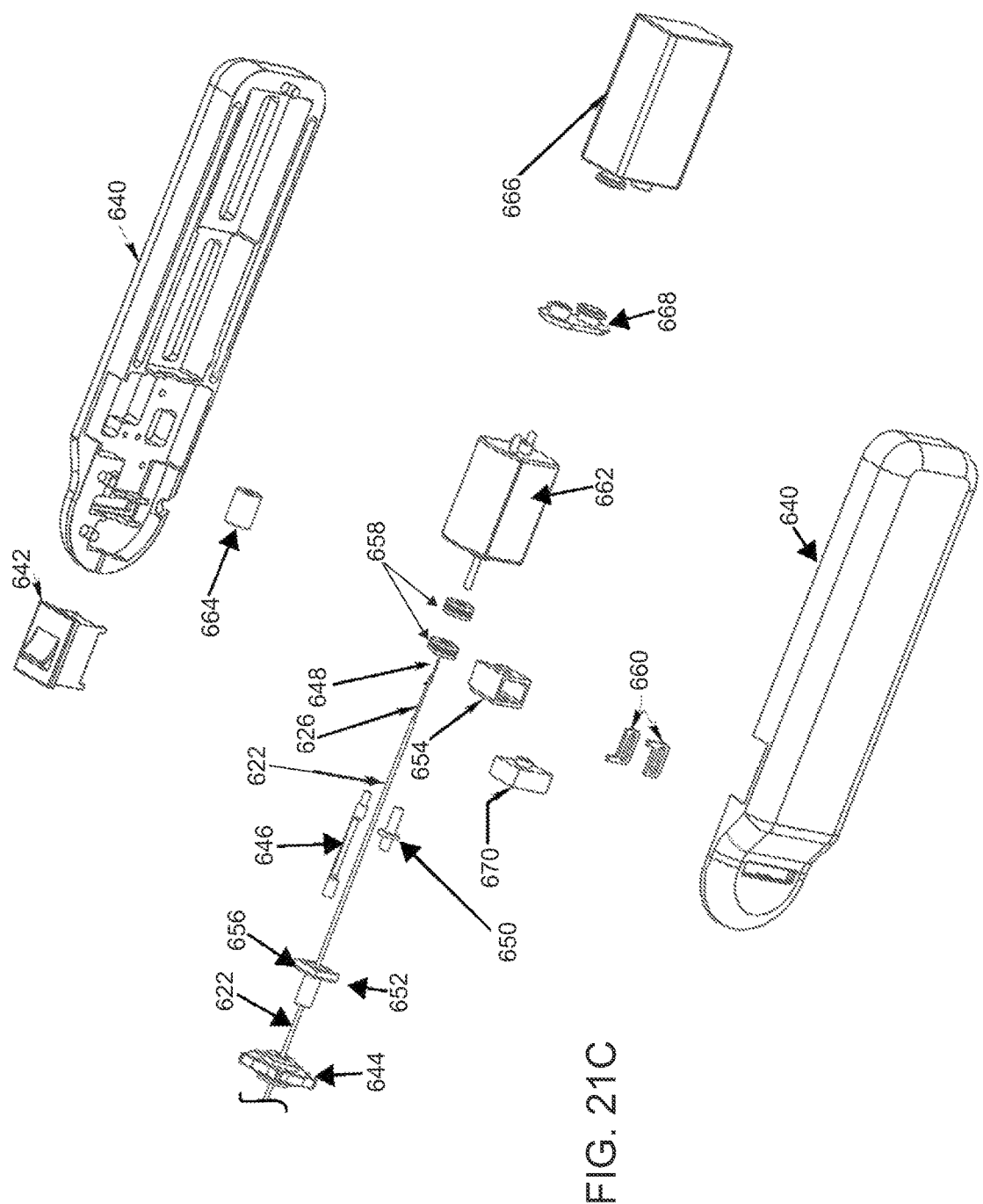
FIG. 21C is a component view of the motorized trephine device in FIGS. 21A to 21B.

FIGS. 21A to 21D depict the proximal housing 640 of the trephine device 610. As depicted in FIGS. 21A and 21B, the proximal housing comprises a power switch 642 and an adjustment interface 644. The trephine device 610 may be provided with a single speed motor which is turned on or off by the power switch 642, but in other configuration, the power switch may be replaced with a slide, knob or other variable setting controller. The adjustment interface 644 comprises a rotatable wheel which may be used to extend or withdrawal the drive shaft 626 with respect to the distal surface 618 of the trephine device 610. The insertion ports for the guidewire lumen and the scope lumen are not depicted in FIGS. 21A and 21B.

Figure 21D:
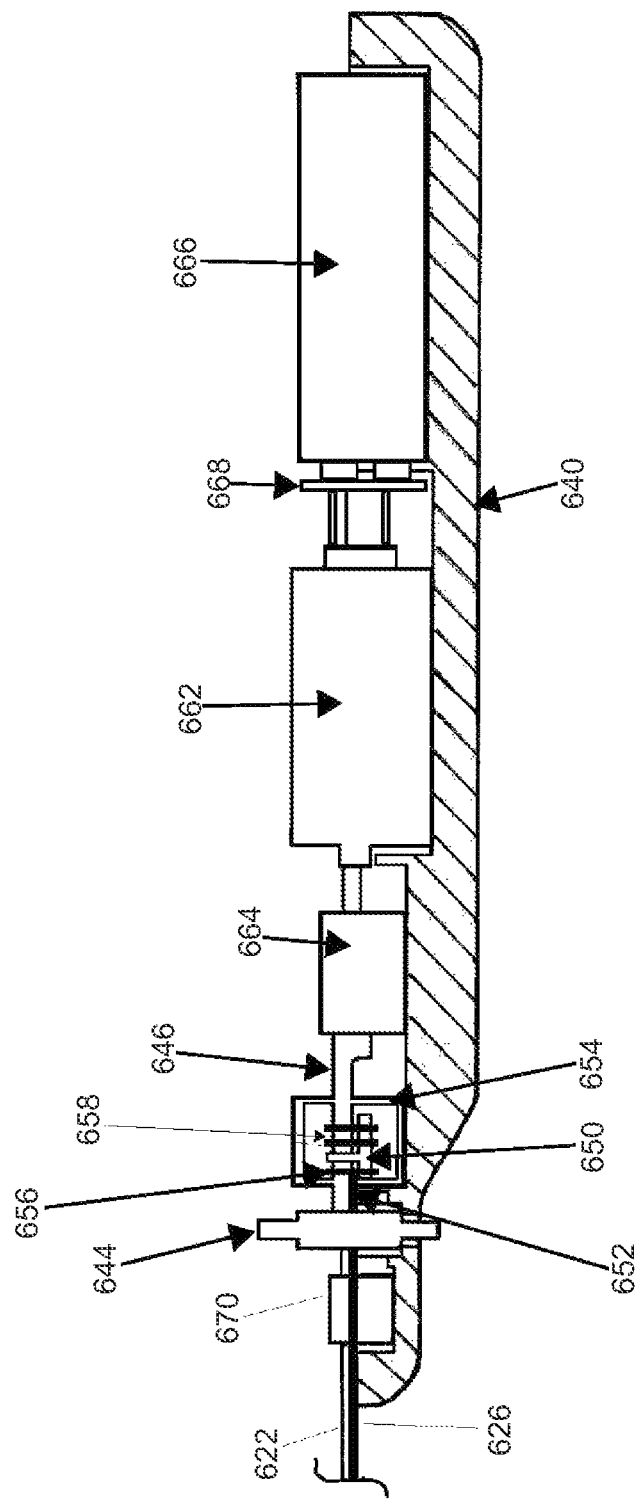
FIG. 21D is a cross-sectional view of the tissue disrupting apparatus in 21A and 21B with a portion of the housing removed.

Referring to FIGS. 21C and 21D, the components within housing 640 of trephine device 610 from FIGS. 21A and 21B are described. FIG. 21C is a component view of the internal components of housing 540, while FIG. 21D is a schematic cross-sectional view with a portion of housing 640 removed. As shown in FIG. 21D, the drive shaft 626 of the cutting assembly is coupled to an open shaft 646, while an adjustment member 648 which controls the extension of the cutting assembly extends from the drive shaft 626 and is attached to a drive key 650. A seal 670 may be used to protect the contents of the housing from any contaminants. The adjustment interface 644 is movably coupled to a thrust member 650 so that the rotation of adjustment interface 644 results in axial movement of thrust member 650. In some embodiments, the thrust member 652 may be configured with helical threads that are complementary to threads on the adjustment interface 644. In other embodiments, however, other structures for manipulating thrust member 652 may be used, including a slide or a pivot member. Thrust member 652 acts on drive key 650 by a coupling structure 654 which is configured to movably couple the thrust member 652 to the drive key 650. The coupling structure 654 permits the rotation of the drive shaft 626 while also coupling the axial movements of the thrust member 652 to the drive key 650 to extend or withdraw the cutting assembly. The thrust member 652 may comprise a flange 656 to facilitate retention of the thrust member 652 with coupling structure 654. The flange 656 may comprise a bearing to facilitate any rotational movement of drive key 650 against the flange 656. The coupling structure 654 may also contain one or more retaining bearings 658 to facilitate rotation of the drive shaft 626 and the drive key 650 while transmitting any axial forces to drive key 650. The coupling structure 654 is optionally provided with one or more limiters 660, which may be used to limit the extension of the cutting assembly. The drive shaft 626 may be directly coupled to the motor 662, or coupled using a coupler 664. The coupler 664 may be configured to permit some axial movement of drive shaft 626 in embodiments where drive shaft 626 is directly coupled to a control interface for manipulating the cutting assembly. The trephine device 610 may be powered using a battery 666 that is coupled to the motor 662 by a battery connector 668. As depicted in FIG. 21C, battery 610 may be a standardized battery such as a 9-volt battery, or a custom battery.

Although the proximal ports for the various lumens of the shaft 626 are not depicted in FIGS. 21C and 21D for purposes of clarity, these proximal ports may attach to their respective lumens of the shaft 626 at any position at or proximal to the housing seal 670 and even along the shaft 626 directly in a position distal to the proximal housing 640. In some further example, the guide wire lumen of the trephine device may comprise a short-length, rapid-exchange type lumen about the distal end of the shaft 626.

FIGS. 22A to 22D depict one exemplary method for using a trephine device. The guidewire 600 is anchored at an anchoring site of 700 about or at the targeted tissue removal site 702. In some examples, the anchoring site and the tissue removal site are the same site or are overlapping sites, while in other examples, the two sites may be non-overlapping. The penetration depth of the guidewire 600 may be adjusted to permit the desired degree of tissue removal. The depth may be set prior to the insertion of the trephine device 610, but may also be adjusted later in the procedure. Once the guidewire 600 is secured to the anchoring site 700, the trephine device 610 is passed over the guidewire using the guidewire lumen 612. As the trephine device 610 is inserted, a fiberoptic scope, rod lens scope, or other viewing system may be inserted into the trephine device 610 is able to view the surrounding tissues using the viewing aperture 620, and to identify structures such as the spinal nerve 704. In other examples, the viewing system may be integrally formed with the trephine device. The tissue removal path or site may be compared to the position of the spinal nerve 704 to confirm that a safe distance is kept from the nerve 704.

Figure 22A:
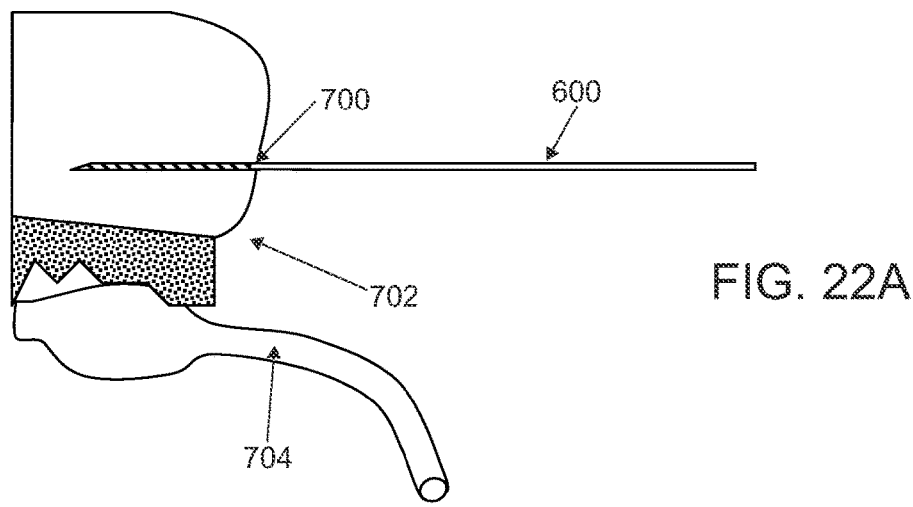
Figure 22B:
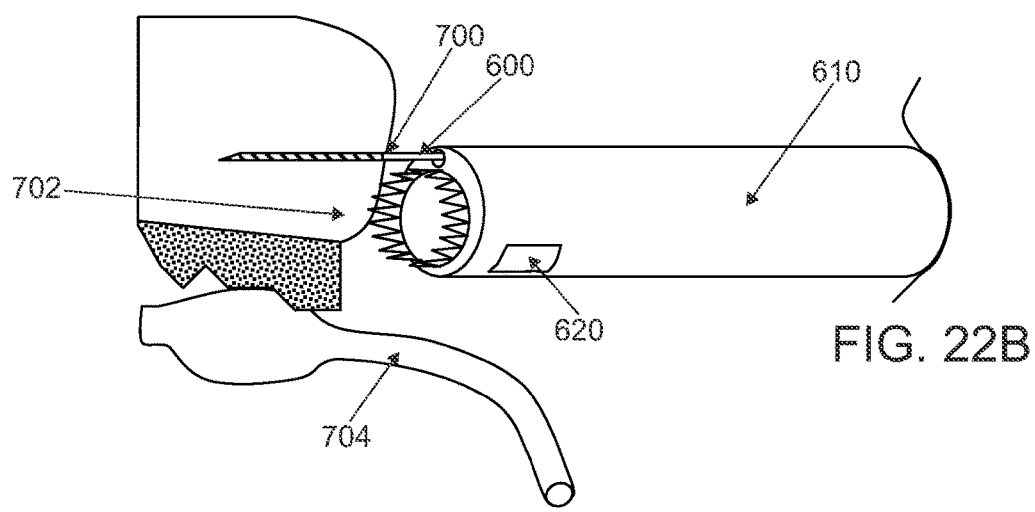
Figure 22C:
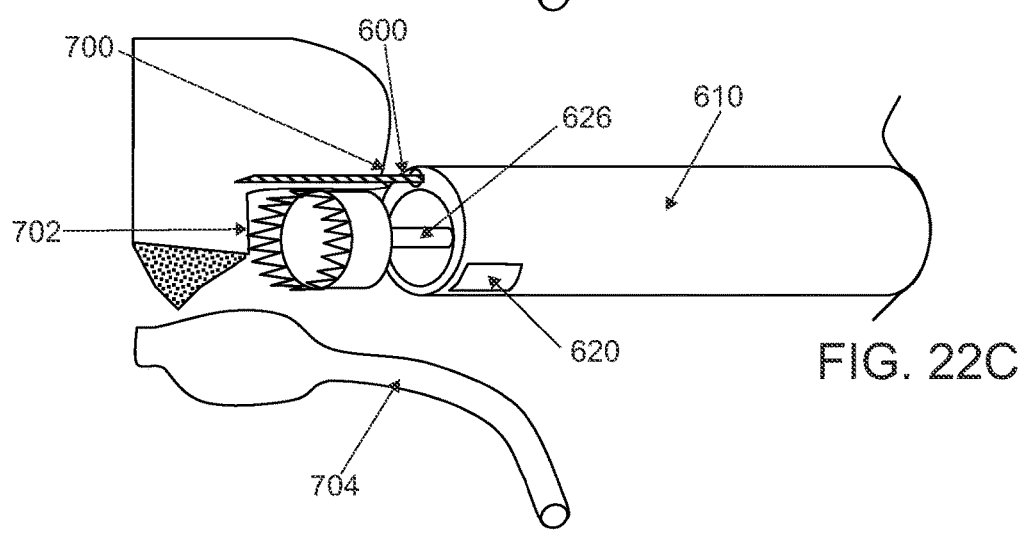

As tissue or bone is removed from the tissue removal site 702, the trephine device 610 is adjusted to extend the drive shaft 626 distally to remove more tissue, as shown in FIG. 22C. Once the desired amount or outcome is achieved, the trephine device and the guidewire may be removed. In other embodiments, additional instruments may be inserted over the guidewire to further inspect, diagnose, or treat the tissues about the guidewire.

As illustrated in FIG. 22D, in some procedures where a large site of tissue removal is desired, the trephine device may be rotated about its guidewire lumen 612 from the first tissue removal site 702 to removal tissue at other sites 706 in a circular pattern around the guidewire lumen 612. This technique may be used where the guidewire lumen 612 is not located within the cutting assembly 614.

Figure 23A:
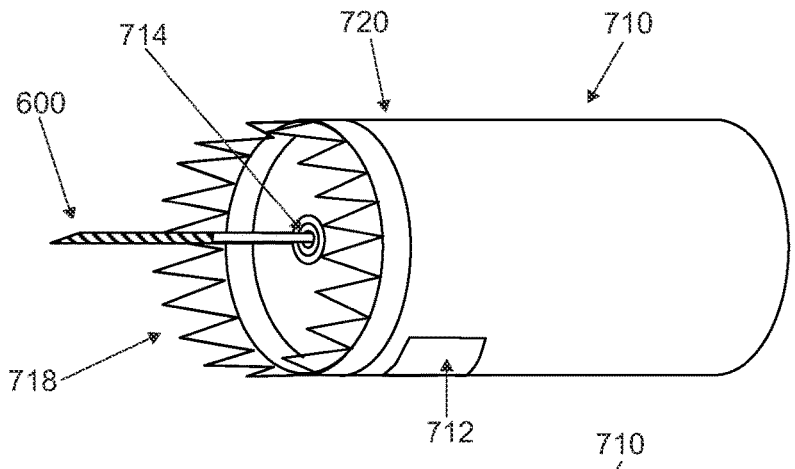
FIG. 23A depicts another embodiment of a trephine.
Figure 23B:
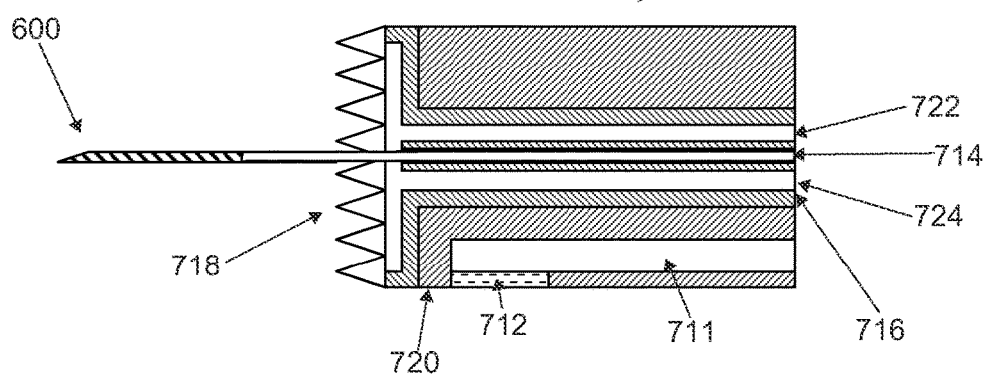
FIG. 23B is a cross-sectional view of the trephine in FIG. 23A.

FIGS. 23A and 23B depict another embodiment of a trephine device 710, comprising a scope lumen 711 with viewing aperture 712 and a guidewire lumen 714 located within the drive shaft 716 of the cutting assembly 718. This particular configuration permits the placement of the guidewire 600 directly in the target tissue site, and does not require that the user determine how far away the guidewire 600 should be anchored from the target site. The cutting assembly 718 also comprises one or more accessory lumens 722 and 724, which may be used to deliver therapeutic agents or to irrigate or suction the tissue removal site.

Although this embodiment of the trephine device 700 is also rotatable or movable about a drive shaft 716, in one variant embodiment, the cutting assembly may be fixed to the shaft 720 of the trephine device 712 and the entire shaft 720 is manipulated to core out tissue. This variant embodiment has less moving parts and may augment the tactile responsiveness of the procedure compared to other embodiments.

Figure 24:
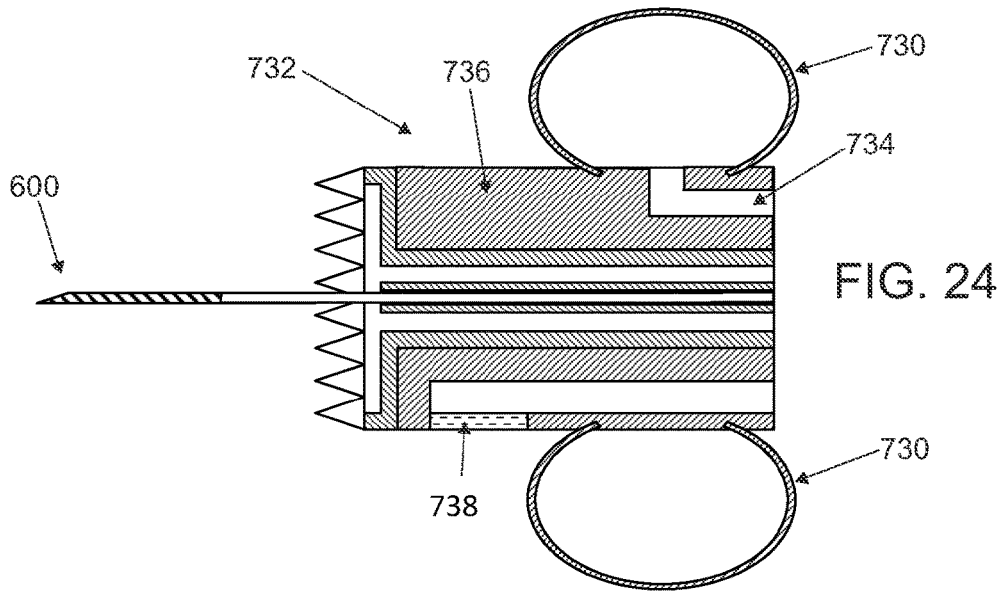
FIG. 24 depicts another embodiment of a trephine with an inflatable balloon.

FIG. 24 depicts another variant embodiment wherein an inflatable balloon 730 is provided on the trephine device 732. The balloon 730 may be inflated using an inflation lumen 734 of the trephine shaft 736. The balloon 730 may have any of a variety of shapes and may be located in any of a variety of positions and site along the shaft 736. Although the balloon 730 in FIG. 24 is located proximal to the viewing aperture 738, in other embodiments, the balloon may be located distal to the aperture 738 or surrounding the aperture 738. The balloon may have a circumferential configuration about the shaft 736, but may also comprise a partial circumference or may be eccentrically positioned with respect to the shaft 736.

FIG. 25A illustrates another embodiment comprising a trephine device 750 with a variable guidewire lumen 752. In this particular embodiment, the guidewire 600 may have a range of locations within the guidewire lumen 752, which may provide a range of distances from the cutting assembly 754, or to adjust the focus distance from the viewing window 768 to a particular structure. Referring to FIGS. 25B and 25C, to control the location of the guidewire 600 within the guidewire lumen 752, forces acting through one or more bias members 756 and 758 may be adjusted to move the guidewire 600. Here one bias member 756 is fixed to the lumen 752 at is two ends 760 and 762, while the other bias member 758 has a distal fixed end 764 and an adjustable proximal end 7. By adjusting the axial tension of the adjustable bias member 758, the net balance of forces acting on the guidewire 600 may shift the guidewire 600 to a different location. Thus, the variable guidewire lumen 752 may be used to adjust the distance of the cutting assembly 754 from other body structures.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

What is claimed as new and desired to be protected by Letters Patent of the United States is:

1. A system, comprising:
    a cannula body with a proximal end, a distal end, a guide lumen, a drive shaft lumen, and a scope lumen;
    a drive shaft, the drive shaft lumen configured to receive the drive shaft;
    a trephine coupled to the drive shaft;
    a guidewire, the guide lumen configured to receive the guidewire, the guidewire including a threaded distal end configured to attach to bony tissue; and
    a viewing apparatus, the scope lumen configured to receive the viewing apparatus,
    the scope lumen ending in a closed distal end within the cannula body, and including a distal viewing aperture in a longitudinal sidewall of the cannula body, such that a longitudinal axis of the scope lumen is generally parallel to a length of the distal viewing aperture.

2. The system of claim 1, wherein the guide lumen is located within the driveshaft.

3. The system of claim 1, wherein the trephine is a rotatable trephine with a rotation axis.

4. The system of claim 3, wherein the trephine is configured with a rotation range of less than about 15 degrees.

5. The system of claim 4, wherein the trephine is coupled to a reciprocation assembly.

6. The system of claim 3, wherein the rotatable trephine is coupled to a motor.

7. The system of claim 3, wherein on an axial-cross section, the guide lumen is located a distance from the rotation axis of the rotatable trephine, the distance being equal to or greater than about the radius of the rotatable trephine.

8. The system of claim 1, wherein the trephine has a fixed position relative to the cannula body.

9. The system of claim 1, further comprising a handle attached to the cannula body.

10. The system of claim 1, wherein the guide lumen comprises at least one deformable tension element.

11. The system of claim 10, wherein the guide lumen comprises at least two deformable tension elements.

12. The system of claim 11, wherein one of the at least two deformable tension elements is user-controlled.

13. The system of claim 1, wherein the viewing apparatus includes at least one fiber optic.

14. The system of claim 1, wherein the viewing apparatus is a fiber optic scope.

15. The system of claim 1, wherein the distal viewing aperture is covered by a transparent material.

16. The system of claim 1, wherein the distal viewing aperture is located at the closed distal end of the scope lumen.

* * * * *